(12) United States Patent
Kawamura et al.

(10) Patent No.: US 8,864,700 B2
(45) Date of Patent: Oct. 21, 2014

(54) HEAT EXCHANGER AND HEAT-EXCHANGER-INTEGRATED OXYGENATOR

(75) Inventors: Shin-ichi Kawamura, Osaka (JP); Kazuhisa Ishihara, Osaka (JP); Naoaki Yasumura, Osaka (JP)

(73) Assignee: Nipro Corporation, Osaka (JP)

( * ) Notice: Subject to any disclaimer, the term of this patent is extended or adjusted under 35 U.S.C. 154(b) by 106 days.

(21) Appl. No.: 13/578,827

(22) PCT Filed: Feb. 15, 2011

(86) PCT No.: PCT/JP2011/053074
§ 371 (c)(1),
(2), (4) Date: Aug. 14, 2012

(87) PCT Pub. No.: WO2011/099610
PCT Pub. Date: Aug. 18, 2011

(65) Prior Publication Data
US 2012/0308434 A1    Dec. 6, 2012

(30) Foreign Application Priority Data
Feb. 15, 2010  (JP) .................... 2010-030297

(51) Int. Cl.
*A61M 37/00*    (2006.01)
*A61M 1/16*    (2006.01)
*B01D 63/02*    (2006.01)
*F28D 7/16*    (2006.01)
*F28D 21/00*    (2006.01)
*F28F 9/02*    (2006.01)

(52) U.S. Cl.
CPC ............ *A61M 1/1698* (2013.01); *F28D 7/1607* (2013.01); *B01D 63/02* (2013.01); *B01D 2313/21* (2013.01); *F28D 2021/005* (2013.01); *F28F 9/0265* (2013.01)
USPC .......................... 604/6.13; 604/4.01; 604/5.01

(58) Field of Classification Search
CPC .................. A61M 1/1698; A61M 2001/1629; A61M 1/369; A61M 5/44
USPC ................................................. 604/4.01, 6.13
See application file for complete search history.

(56) References Cited

U.S. PATENT DOCUMENTS 4,791,054 A * 12/1988 Hamada et al. .................. 435/2
5,294,397 A * 3/1994 Oshiyama et al. ............ 264/251

(Continued)

FOREIGN PATENT DOCUMENTS

JP    11-47269 A    2/1999
JP    11-508476 A    7/1999

(Continued)

*Primary Examiner* — Leslie Deak
(74) *Attorney, Agent, or Firm* — Birch, Stewart, Kolasch & Birch, LLP

(57) ABSTRACT

A plurality of heat transfer pipes have a circumferential portion arranged at a short distance from an inner surface of a heat exchanger case while they are bundled to form a pipe group and a first chord which retracts toward a center in a direction of cylinder diameter from an arc formed by the circumferential portion. The plurality of bundled heat transfer pipes are loaded in the exchange case such that the first chord and an inner surface of the heat exchange case on a side where a heat exchange medium inlet port is attached are opposed to each other. By making a flow of a heat exchange medium to each heat transfer pipe uniform, a heat exchanger capable of obtaining high heat exchange performance is obtained.

5 Claims, 14 Drawing Sheets

(56) References Cited

U.S. PATENT DOCUMENTS

| | | |
|---|---|---|
| 5,823,987 A | 10/1998 | Elgas et al. |
| 6,004,511 A | 12/1999 | Biscegli |
| 7,749,435 B2 * | 7/2010 | Ogihara et al. ......... 422/46 |
| 2007/0217948 A1 | 9/2007 | Ghelli et al. |
| 2010/0272604 A1 * | 10/2010 | Carpenter et al. ......... 422/45 |

FOREIGN PATENT DOCUMENTS

| | | |
|---|---|---|
| JP | 2001-507245 A | 6/2001 |
| JP | 2007-244880 A | 9/2007 |

* cited by examiner

HEAT EXCHANGER AND HEAT-EXCHANGER-INTEGRATED OXYGENATOR

TECHNICAL FIELD

The present invention relates to a heat exchanger and a heat-exchanger-integrated oxygenator, and particularly to a multipipe heat exchanger and a heat-exchanger-integrated oxygenator capable of removing carbon dioxide from blood, adding oxygen to the blood, and adjusting a temperature of the blood during extracorporeal circulation of blood.

BACKGROUND ART

Japanese National Patent Publication No. 11-508476 (PTL 1) discloses an oxygenator including a generally cylindrical heat exchanger (of a multipipe type), a blood inlet manifold communicating with a lower end of the heat exchanger, a transition manifold communicating with an upper end of the heat exchanger, a generally cylindrical membrane-type oxygenator concentrically surrounding the heat exchanger and communicating with the transition manifold, and a blood outlet manifold communicating with the membrane-type oxygenator. According to PTL 1, performance as the oxygenator can be enhanced by improving various components constituting the oxygenator.

CITATION LIST

Patent Literature

PTL 1: Japanese National Patent Publication No. 11-508476

SUMMARY OF INVENTION

Technical Problem

An object of the present invention is to provide a heat exchanger and a heat-exchanger-integrated oxygenator capable of obtaining high heat exchange performance by making flow of a heat exchange medium to each heat transfer pipe uniform.

Solution to Problem

A heat exchanger according to a first aspect of the present invention is a multipipe heat exchanger used for extracorporeal circulation of blood. The heat exchanger includes a heat exchanger case, a plurality of heat transfer pipes, a heat exchange medium inlet port, and a heat exchange medium outlet port.

The heat transfer pipe is loaded in the inside of the heat exchanger case. The heat exchange medium inlet port has a shape of a straight pipe. The heat exchange medium inlet port is attached to an outer surface on a one end side of the heat exchanger case such that an extension of a pipe axis crosses a cylinder axis of the heat exchanger case and the extension extends toward the other end side of the heat transfer pipe. The heat exchange medium inlet port supplies a prescribed heat exchange medium to an outer surface of the heat transfer pipe.

The heat exchange medium outlet port is attached to the outer surface of the heat exchanger case, on a side opposite in a direction of cylinder diameter of the heat exchanger case to a position where the heat exchange medium inlet port is attached. The heat exchange medium outlet port discharges the heat exchange medium supplied to the outer surface of the heat transfer pipe.

The plurality of heat transfer pipes in a bundled state have a circumferential portion and a first chord. The circumferential portion is arranged at a short distance from an inner surface of the heat exchanger case. The first chord retracts toward a center in the direction of cylinder diameter from an arc formed by the circumferential portion.

The plurality of heat transfer pipes in the bundled state are loaded in the inside of the heat exchanger case such that the first chord and the inner surface of the heat exchanger case on a side where the heat exchange medium inlet port is attached are opposed to each other.

A heat exchanger according to a second aspect of the present invention relies on the heat exchanger according to the first aspect above, and the inner surface of the heat exchanger case on the side where the heat exchange medium inlet port is attached is formed substantially in such a tapered shape as gradually protruding toward the center in the direction of cylinder diameter such that a distance from the first chord is smaller from the one end side of the heat exchanger case toward the other end side of the heat exchanger case.

A heat exchanger according to a third aspect of the present invention relies on the heat exchanger according to the first aspect above, and the plurality of heat transfer pipes in the bundled state further have a second chord which retracts toward the center in the direction of cylinder diameter from the arc formed by the circumferential portion, on a side opposite in the direction of cylinder diameter to the first chord.

A heat exchanger according to a fourth aspect of the present invention relies on the heat exchanger according to the first aspect above, and the inner surface of the heat exchanger case on a side where the heat exchange medium outlet port is attached is formed substantially in such a tapered shape as gradually protruding toward the center in the direction of cylinder diameter such that a distance from the second chord is smaller from the one end side of the heat exchanger case toward the other end side of the heat exchanger case.

A heat-exchanger-integrated oxygenator according to the present invention includes the heat exchanger according to the first aspect above, a bottom member, gas exchange means, and a blood outlet port. The bottom member has a blood inlet port. The bottom member is attached to one end of the heat exchanger case. The gas exchange means communicates with the other end of the heat exchanger case. Through the gas exchange means, the blood that flowed out of the other end of the heat transfer pipe flows. The blood outlet port communicates with the gas exchange means. The blood outlet port discharges the blood that flowed through the gas exchange means.

Advantageous Effects of Invention

According to the present invention, a heat exchanger and a heat-exchanger-integrated oxygenator capable of obtaining high heat exchange performance by making flow of a heat exchange medium to each heat transfer pipe uniform can be obtained.

DESCRIPTION OF EMBODIMENTS

Figure 1:
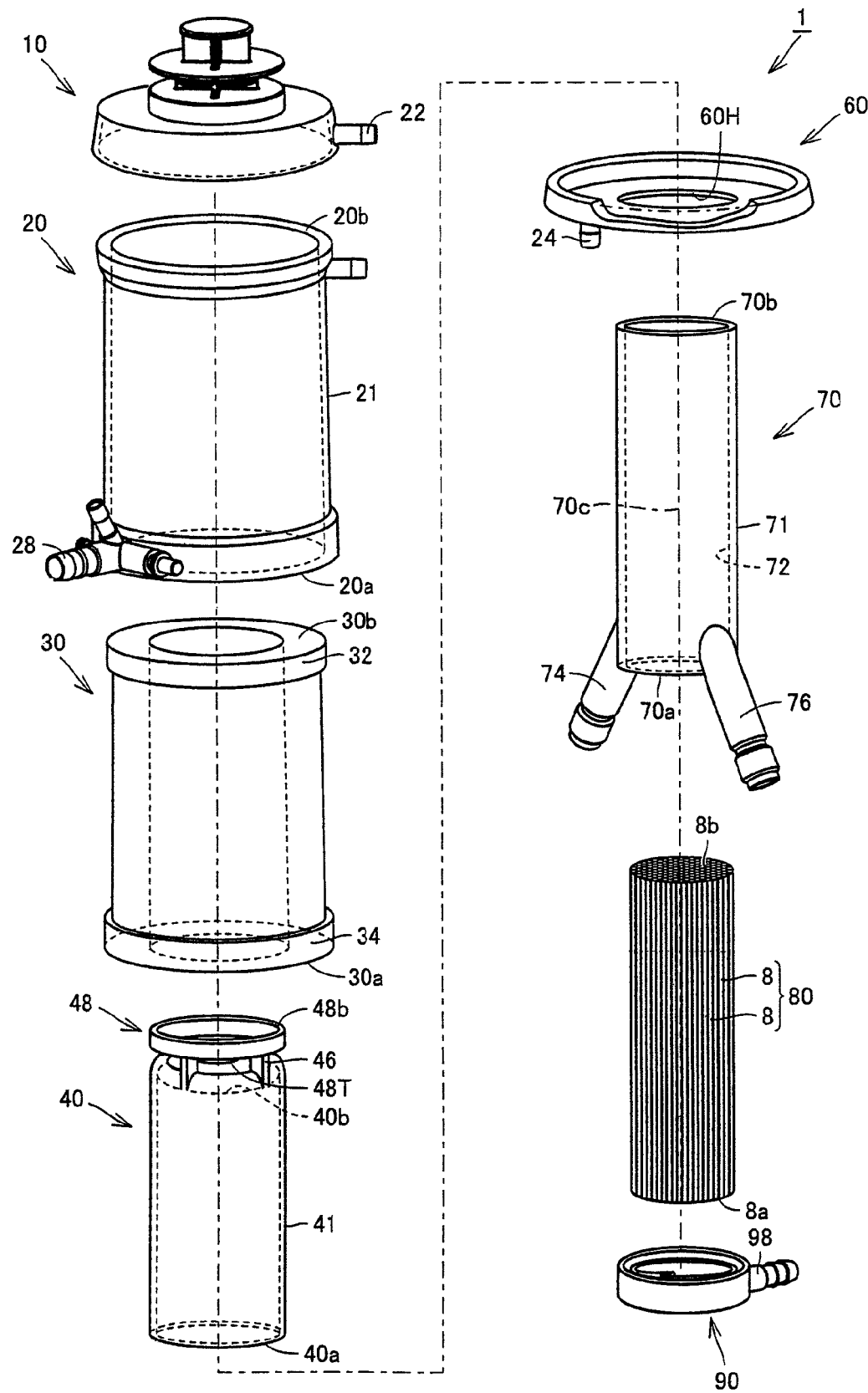
FIG. 1 is a perspective view showing various components constituting a heat-exchanger-integrated oxygenator in an embodiment.

A heat exchanger and a heat-exchanger-integrated oxygenator in an embodiment according to the present invention will be described hereinafter with reference to the drawings. When the number, an amount or the like is mentioned in the embodiment below, the scope of the present invention is not necessarily limited to the number, the amount or the like, unless otherwise specified. In the embodiment described below, the same or corresponding elements have the same reference characters allotted and redundant description may not be repeated.

(Heat-Exchanger-Integrated Oxygenator 1)
(Overall Construction)

An overall construction of a heat-exchanger-integrated oxygenator 1 will be described with reference to FIG. 1. Heat-exchanger-integrated oxygenator 1 includes a first header 10, a housing 20, a bundle 30, a cylindrical core 40, a second header 60, a heat exchanger case 70, a pipe group 80, and a bottom member 90. Though second header 60 is shown in a partially exploded manner, such a part is actually continuous.

Details of various components constituting heat-exchanger-integrated oxygenator 1 will be described below, and "gas exchange means" in the present invention is constructed to include a gas inlet port 22 provided in first header 10, bundle 30, and a gas outlet port 24 provided in second header 60. "Heat exchange medium supply means" in the present invention is constructed to include a heat exchange medium inlet port 74 provided in heat exchanger case 70 and a heat exchange medium outlet port 76 provided in heat exchanger case 70.

First header 10 is formed like a cap. First header 10 is provided with gas inlet port 22 extending in a direction of normal. Gas inlet port 22 communicates with the inside of first header 10. Gas inlet port 22 is coupled to a prescribed tube (not shown) for supply of a gas (such as an oxygen gas).

Housing 20 is formed in a cylindrical shape. Housing 20 is fitted into first header 10 from the other end 20b side.

On an outer surface 21 on a one end 20a side of housing 20, a blood outlet port 28 is provided. Blood outlet port 28 communicates with the inside of housing 20. Blood outlet port 28 is coupled to a prescribed tube (not shown) for returning blood to a patient.

Bundle 30 is formed in a cylindrical shape as a hollow fiber membrane formed like a mat is wound around an outer surface 41 of cylindrical core 40 which will be described next. On the other end 30b side of bundle 30, an annular sealing member 32 is provided. On one end 30a side of bundle 30, another annular sealing member 34 is provided. Gas inlet port 22 provided in first header 10 communicates with each inside of the hollow fiber membrane in bundle 30 (details of which will be described later). Bundle 30 is fitted into housing 20 from the other end 30b side, while it is wound around cylindrical core 40.

Cylindrical core 40 is formed in a cylindrical shape. A diffusion portion 48 is provided on the other end 40b side of cylindrical core 40. Diffusion portion 48 deflects a flow of blood that has flowed out of pipe group 80, outward in a direction of cylinder diameter, and diffuses the blood outward in the direction of cylinder diameter (details of which will be described later with reference to FIG. 4). Diffusion portion 48 is connected to a main body portion side of cylindrical core 40 with a plurality of support ribs 46 extending in an up/down direction over the sheet surface being interposed. Diffusion portion 48 may be formed integrally with cylindrical core 40 or may be attached to cylindrical core 40 after it is molded as a separate part. In a lower central portion of diffusion portion 48, a substantially conical protruding portion 48T protruding inward into cylindrical core 40 (downward over the sheet surface) is provided (see FIG. 20).

Cylindrical core 40 is fitted into housing 20 from the other end 48b side, together with bundle 30. A portion surrounded by the other end 40b side of cylindrical core 40, support rib 46, and diffusion portion 48 (see an outlet portion 47 in FIG. 20) communicates with the inside of cylindrical core 40. The portion (outlet portion 47) communicates with each outer surface of the hollow fiber membrane in bundle 30 while cylindrical core 40 and bundle 30 are fitted into housing 20 (see FIG. 21). Other detailed constructions of cylindrical core 40 and diffusion portion 48 will be described later with reference to FIGS. 20 and 21.

After bundle 30 and cylindrical core 40 are fitted into housing 20, one end 20a of housing 20 is closed by cap-shaped second header 60. Second header 60 has an opening 60H in the center. Heat exchanger case 70 which will be described next is fitted into opening 60H. Gas outlet port 24 is provided on a lower surface side of second header 60. Gas outlet port 24 communicates with the inside of second header 60. Gas outlet port 24 may be coupled to a prescribed tube (not shown) for exhausting a gas from the inside to the outside of housing 20.

Heat exchange medium inlet port 74 and heat exchange medium outlet port 76 are attached to an outer surface 71 on a one end 70a side of heat exchanger case 70. Heat exchange medium inlet port 74 and heat exchange medium outlet port 76 are located on opposing sides in a direction of cylinder diameter, respectively. Heat exchange medium inlet port 74 and heat exchange medium outlet port 76 communicate with the inside of heat exchanger case 70.

Heat exchange medium inlet port 74 is coupled to a prescribed tube (not shown) for supplying a heat exchange medium (such as water) set to a prescribed temperature to the inside of heat exchanger case 70. Heat exchange medium outlet port 76 is coupled to a prescribed tube (not shown) for discharging a heat exchange medium from the inside to the outside of heat exchanger case 70. Other detailed constructions of heat exchanger case 70 will be described later with reference to FIG. 14.

Pipe group 80 is constituted of a plurality of thin heat transfer pipes 8. The plurality of heat transfer pipes 8 are bundled substantially in a columnar shape along a central cylinder axis 70c of heat exchanger case 70. The plurality of heat transfer pipes 8 are loaded in the inside of heat exchanger case 70 as pipe group 80 while they are bundled. Other detailed constructions of pipe group 80 will be described later with reference to FIG. 14.

Bottom member 90 is formed like a cap. After pipe group 80 is loaded into heat exchanger case 70, bottom member 90 is fitted in one end 70a of heat exchanger case 70.

A blood inlet port 98 extending in a direction of normal is provided in an outer circumferential surface (93d) of bottom member 90. Bottom member 90 communicates with each inside of heat transfer pipe 8 while it is fitted in heat exchanger case 70. Blood inlet port 98 is coupled to a prescribed tube (not shown) for sending blood from a patient. Other detailed constructions of bottom member 90 will be described later with reference to FIGS. 5 to 7.

Figure 2:
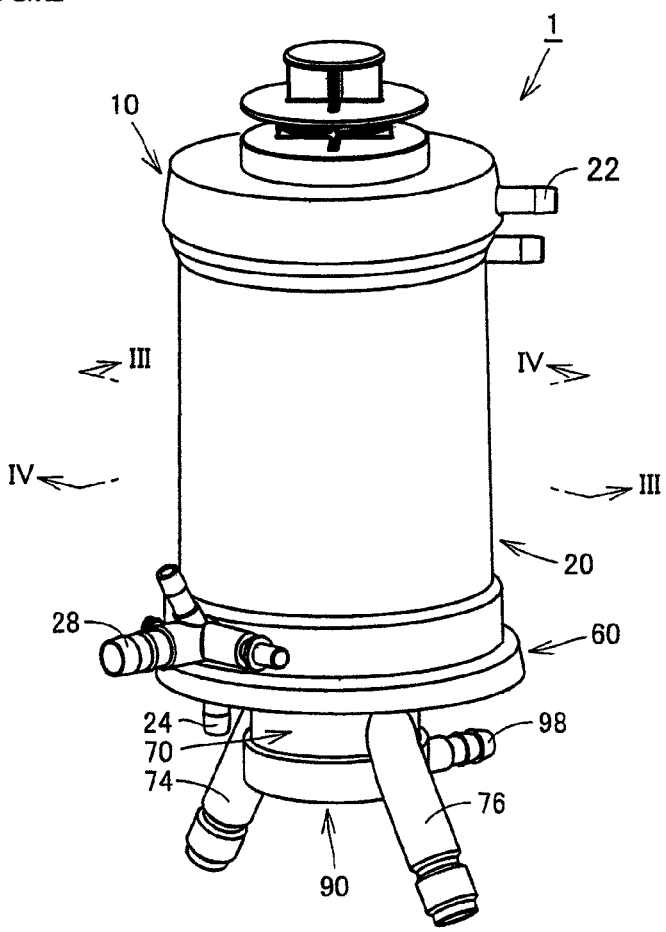
FIG. 2 is a perspective view showing the heat-exchanger-integrated oxygenator in the embodiment.

Referring to FIG. 2, heat-exchanger-integrated oxygenator 1 is constituted by combining first header 10, housing 20, bundle 30 (see FIG. 1), cylindrical core 40 (see FIG. 1), second header 60, heat exchanger case 70, pipe group 80 (see FIG. 1), and bottom member 90 with one another.

(Function of Heat-Exchanger-Integrated Oxygenator 1)

Figure 3:
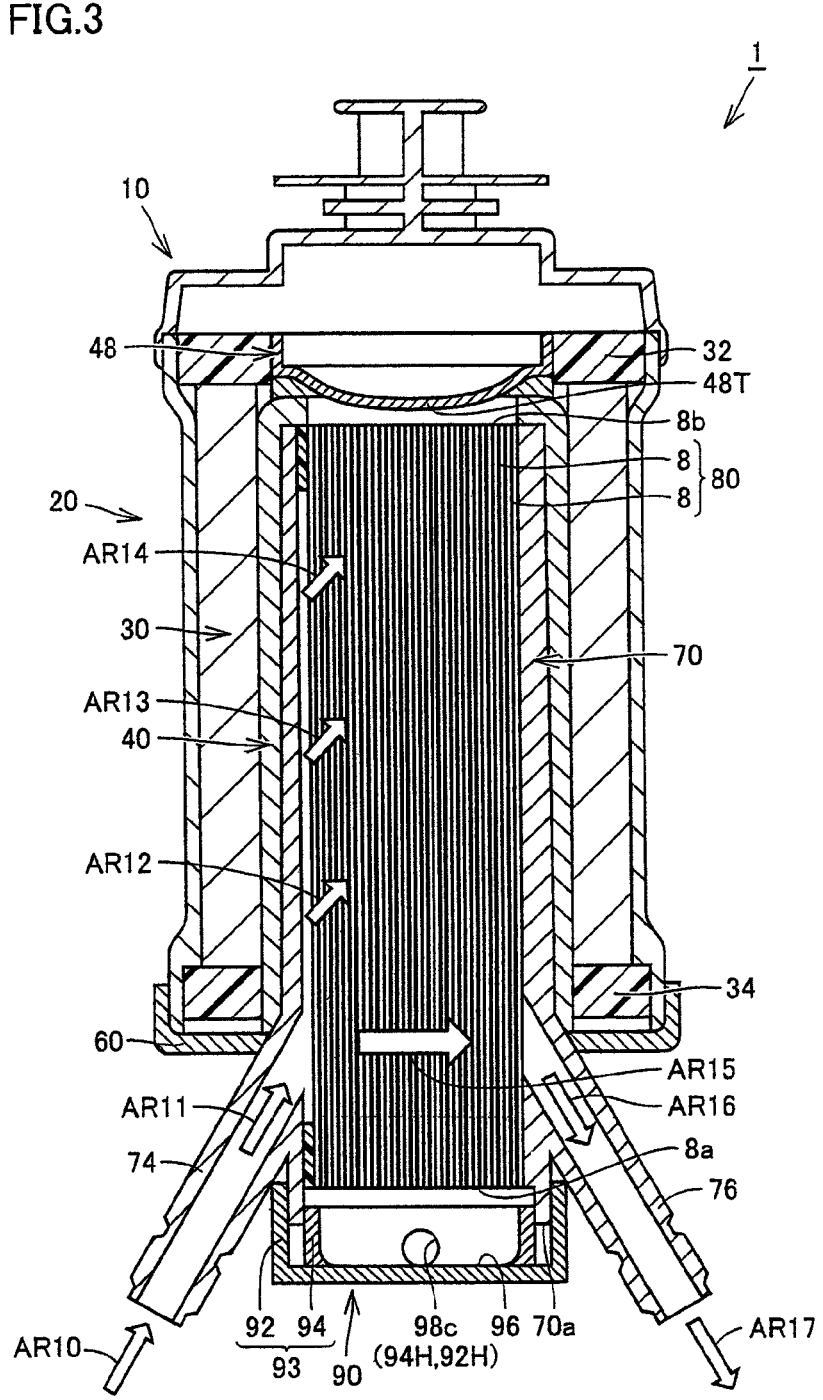
FIG. 3 is a cross-sectional view along the line in FIG. 2, when viewed in a direction of an arrow.
Figure 4:
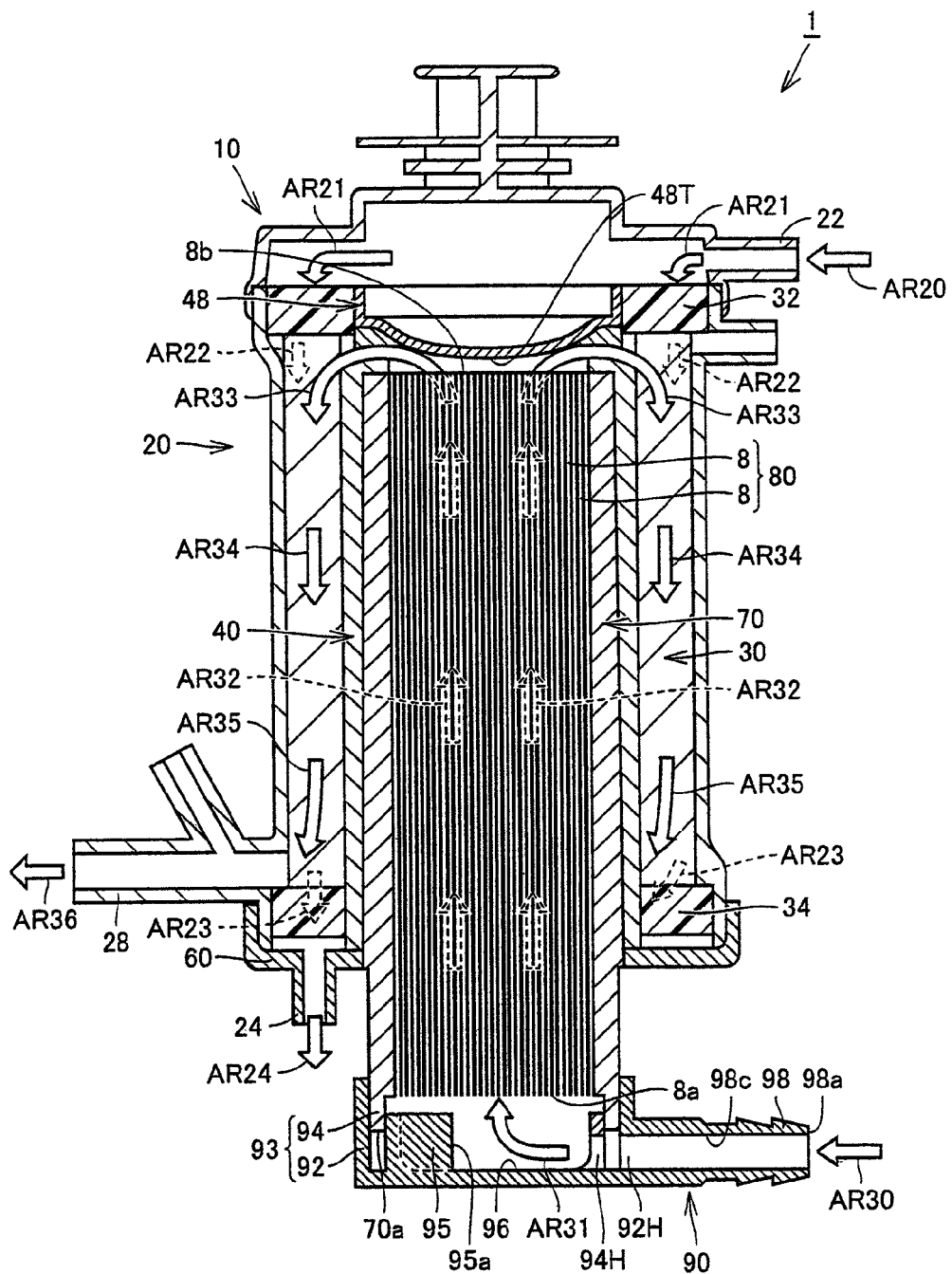
FIG. 4 is a cross-sectional view along the line IV-IV in FIG. 2, when viewed in a direction of an arrow.

A function of heat-exchanger-integrated oxygenator 1 will be described with reference to FIGS. 3 and 4. A flow of a heat exchange medium supplied to heat-exchanger-integrated oxygenator 1 will be described initially with reference to FIG. 3. As shown with an arrow AR10 and an arrow AR11, a heat exchange medium at a prescribed temperature is supplied through heat exchange medium inlet port 74 to the inside of heat exchanger case 70. As shown with an arrow AR12 to an arrow AR14, the heat exchange medium that has reached the inside of heat exchanger case 70 spreads in a direction in parallel to the cylinder axis (the up/down direction over the sheet surface) (details of which will be described later with reference to FIG. 14), and comes in contact with the outer surface of heat transfer pipe 8 in pipe group 80.

The heat exchange medium flows in a direction shown with an arrow AR15 through a gap formed between the outer surfaces of the plurality of heat transfer pipes 8. The heat exchange medium exchanges heat with blood (details of which will be described next) that flows through the inside of heat transfer pipe 8. The heat exchange medium that has completed heat exchange with the blood reaches heat exchange medium outlet port 76 as shown with an arrow AR16. The heat exchange medium is discharged to the outside through heat exchange medium outlet port 76 as shown with an arrow AR17.

A flow of blood supplied to heat-exchanger-integrated oxygenator 1 and a flow of a gas (an oxygen gas being assumed here) will be described next with reference to FIG. 4. As shown with an arrow AR30, blood is supplied through blood inlet port 98 to the inside of bottom member 90. As shown with an arrow AR31, the blood that flowed through the inside of bottom member 90 flows into the inside of heat transfer pipe 8 from one end 8a of heat transfer pipe 8 in pipe group 80. As shown with an arrow AR32, the blood flows from a lower portion of the sheet surface to an upper portion of the sheet surface. As described above, the blood that flows in the inside of heat transfer pipe 8 exchanges heat with the heat exchange medium.

The blood that has reached the other end 8b of heat transfer pipe 8 comes in contact with protruding portion 48T of diffusion portion 48 and it is deflected outward in a direction of cylinder diameter as shown with an arrow AR33. The deflected blood comes in contact with the outer surface of the hollow fiber membrane in bundle 30. The blood passes through a gap formed between the hollow fiber membranes and flows in a direction shown with an arrow AR34 and an arrow AR35.

On the other hand, as shown with an arrow AR20 and an arrow AR21, an oxygen gas is supplied through gas inlet port 22 to a space between first header 10 and the other end 30b of bundle 30. Thereafter, the oxygen gas flows through the inside of the hollow fiber membrane in bundle 30 from the upper portion of the sheet surface to the lower portion of the sheet surface as shown with an arrow AR22 and an arrow AR23.

A partial pressure difference of oxygen and a partial pressure difference of carbon dioxide are generated between the blood that flows over the outer surface of the hollow fiber membrane in a direction shown with arrow AR34 and arrow AR35 and the oxygen gas that flows through the inside of the hollow fiber membrane in a direction shown with arrow AR22 and arrow AR23. As a result of the partial pressure difference, gas exchange is carried out with the hollow fiber membrane being interposed. In the blood, an amount of carbon dioxide decreases while an amount of oxygen increases. In the oxygen gas, an amount of carbon dioxide increases while an amount of oxygen decreases.

As shown with an arrow AR36, the blood is discharged to the outside through blood outlet port 28. As shown with an arrow AR24, the oxygen gas is exhausted to the outside through gas outlet port 24.

As described above, according to heat-exchanger-integrated oxygenator 1, during extracorporeal circulation of blood, carbon dioxide can be removed from the blood, oxygen can be added to the blood, and a temperature of the blood can be adjusted. Though gas exchange between carbon dioxide and oxygen has been described by way of example, according to heat-exchanger-integrated oxygenator 1, gas exchange between other components in the blood and another gas can also be carried out.

(Bottom Member 90)

Figure 5:
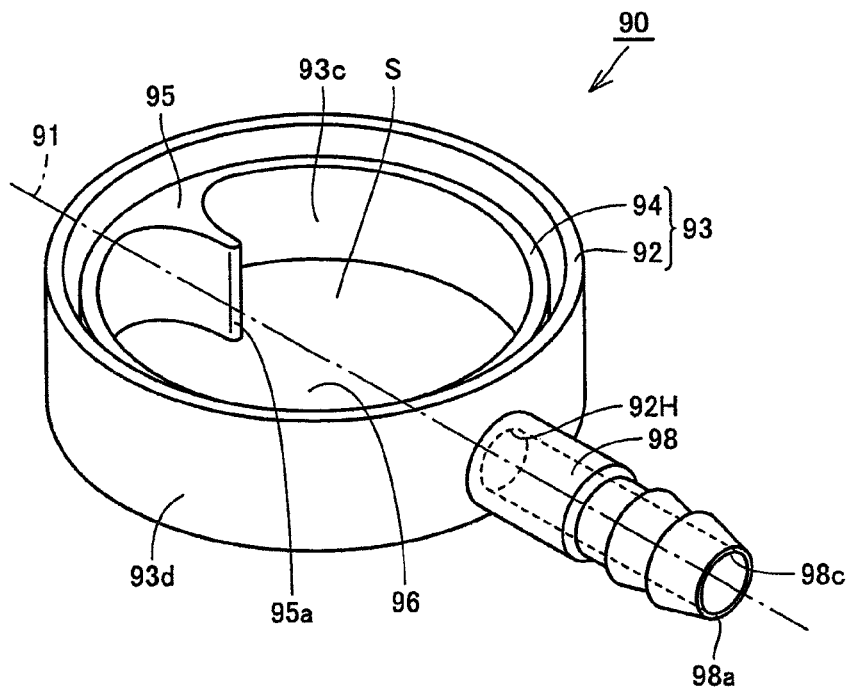
FIG. 5 is a perspective view showing a bottom member used in the heat-exchanger-integrated oxygenator in the embodiment.

Bottom member 90 used in heat-exchanger-integrated oxygenator 1 will be described in detail with reference to FIGS. 5 to 7. Referring mainly to FIG. 5, bottom member 90 has an annular wall 93, a bottom surface 96, blood inlet port 98, and a protrusion 95.

Annular wall 93 is constituted of an outer wall 92 and an inner wall 94. One end 70a of heat exchanger case 70 (see FIG. 3) is fitted in a fluid-tight manner in between outer wall 92 and inner wall 94. Bottom surface 96 is opposed to one end 8a of heat transfer pipe 8 (see FIG. 3). Referring to FIG. 7, bottom surface 96 is arranged to close in a fluid-tight manner, an end portion 92a (on a lower side of the sheet surface) of outer wall 92 and an end portion 94a (on the lower side of the sheet surface) of inner wall 94.

Referring again to FIG. 5, blood inlet port 98 is formed like a pipe. Blood inlet port 98 extends from outer circumferential surface 93d of outer wall 92 of annular wall 93 along a direction of normal 91. Blood inlet port 98 extends such that a pipe axis of blood inlet port 98 and bottom surface 96 are in parallel to each other.

As bottom member 90 is fitted in heat exchanger case 70 (see FIG. 3), a fluid-tight space S is formed inside bottom member 90. An inside 98c of blood inlet port 98 communicates with space S through an opening 92H provided in outer wall 92 and an opening 94H provided in inner wall 94 (see FIGS. 6 and 7).

Protrusion 95 is provided on an inner circumferential surface 93c of inner wall 94 of annular wall 93. Protrusion 95 is opposed to blood inlet port 98 on direction of normal 91. A tip end portion 95a of protrusion 95 stands on bottom surface 96. A side surface of protrusion 95 continues to inner circumferential surface 93c. The side surface of protrusion 95 is formed in a gentle arc toward blood inlet port 98 as it extends from inner circumferential surface 93c to tip end portion 95a of protrusion 95.

(Function and Effect)

Figure 6:
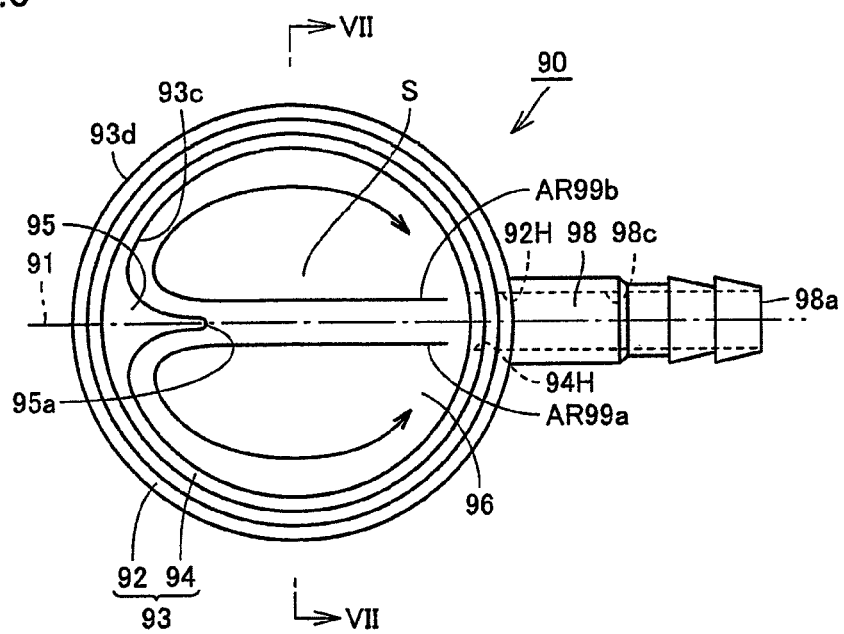
FIG. 6 is a plan view showing the bottom member used in the heat-exchanger-integrated oxygenator in the embodiment.
Figure 7:
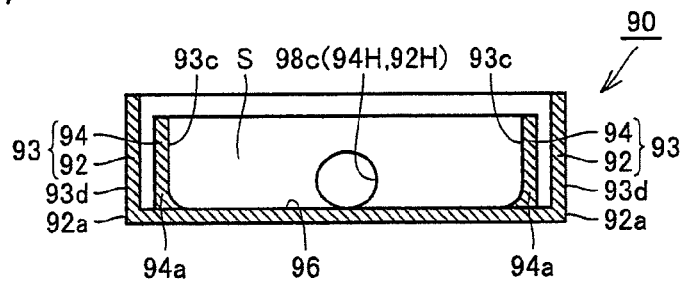
FIG. 7 is a cross-sectional view along the line VII-VII in FIG. 6, when viewed in a direction of an arrow.

Referring to FIG. 6, blood is supplied from a one end 98a side of blood inlet port 98. The blood flows through inside 98c and thereafter reaches space S. After the blood comes in contact with protrusion 95, the blood is gradually deflected by protrusion 95. The blood is divided into two flows, as shown with an arrow AR99a and an arrow AR99b. The blood flows through the inside of space S along inner circumferential surface 93c toward blood inlet port 98. After the inside of space S is filled with the blood, the blood flows into the inside of heat transfer pipe 8 from one end 8a of heat transfer pipe 8 in pipe group 80.

Here, if it is assumed that bottom member 90 does not have protrusion 95, after the blood supplied through blood inlet port 98 reaches space S, the blood comes in contact with opposing inner circumferential surfaces 93c. After the contact, the blood is suddenly deflected along inner circumferential surface 93c. Contact and sudden deflection causes pressure loss in the blood (a contraction/expansion phenomenon). Contact and sudden deflection may destruct cells and thrombocytes in some of the blood.

According to bottom member 90, blood is more gradually deflected by protrusion 95. Occurrence of pressure loss in the blood can be suppressed and destruction of cells and thrombocytes in the blood can also be suppressed. Consequently, with the use of bottom member 90, heat-exchanger-integrated oxygenator 1 achieving further improved performance can be obtained.

(Bottom Member 90A)

A bottom member 90A (a first variation of bottom member 90) that can be used in heat-exchanger-integrated oxygenator 1 will be described with reference to FIGS. 8 and 9. Only a difference from bottom member 90 described above will be described here.

In bottom member 90A, a raised bottom portion 96a, a raised bottom portion 96b, and a groove portion 96c are provided in bottom surface 96. Raised bottom portion 96a and raised bottom portion 96b are preferably disposed on substantially the same plane. Raised bottom portion 96a and raised bottom portion 96b may form substantially a V shape in cross-section such that they gradually incline toward groove portion 96c (in a direction orthogonal to direction of normal 91).

Raised bottom portion 96a and raised bottom portion 96b are arranged at a prescribed distance from each other in a direction orthogonal to direction of normal 91. Raised bottom portion 96a and raised bottom portion 96b are opposed to one end 8a of heat transfer pipe 8 as one end 70a of heat exchanger case 70 (see FIG. 3) is fitted in between outer wall 92 and inner wall 94.

Groove portion 96c is formed substantially in a U shape in cross-section from each end portion close to direction of normal 91 of raised bottom portion 96a and raised bottom portion 96b toward a side opposite to the side where heat exchanger case 70 is fitted (downward over the sheet surface). Groove portion 96c extends along direction of normal 91 from outer wall 92 on a blood inlet port 98 side to inner wall 94 on a protrusion 95 side. Inside 98c of blood inlet port 98 communicates with groove portion 96c.

According to bottom member 90A, the following effect in addition to the effects obtained by bottom member 90 described above can be obtained. The blood supplied from the one end 98a side of blood inlet port 98 to bottom member 90A reaches space S and flows through groove portion 96c. After the blood comes in contact with protrusion 95, it is divided into two flows. The blood is gradually deflected by protrusion 95. The blood flows over each surface of raised bottom portion 96a and raised bottom portion 96b along inner circumferential surface 93c toward blood inlet port 98. An orientation of the blood that flows through groove portion 96c is reverse to an orientation of the blood that flows over each surface of raised bottom portion 96a and raised bottom portion 96b.

If it is assumed here that raised bottom portion 96a, raised bottom portion 96b, and groove portion 96c are not provided in bottom surface 96, the blood supplied through blood inlet port 98 and the blood deflected by protrusion 95 come in contact with each other in the inside of space S (collide with each other). Contact causes a turbulent flow in the blood. Contact may also cause pressure loss.

According to bottom member 90A, the blood that flows through groove portion 96c and the blood that flows over each surface of raised bottom portion 96a and raised bottom portion 96b flow through portions displaced in a direction of height and hence a chance of contact with each other is less. Bottom member 90A can suppress occurrence of a turbulent flow in the blood and occurrence of pressure loss in the blood.

In addition, as raised bottom portion 96a, raised bottom portion 96b, and groove portion 96c are provided in bottom surface 96, a volume of space S in bottom member 90A can be made smaller than a volume of space S in bottom member 90 described above. It is assumed that a position in a direction of height (an up/down direction over the sheet surface in FIG. 9) in the most protruding portion of groove portion 96c of bottom member 90A (a portion on a lower side of the sheet surface) is the same as a position in a direction of height of bottom surface 96 in bottom member 90.

In this case, a volume of space S in bottom member 90A is smaller than a volume of space S in bottom member 90 described above. An amount of blood necessary for filling space S is smaller in bottom member 90A than in bottom member 90. According to bottom member 90A, a priming volume of blood is smaller. Therefore, a priming solution is decreased and dilution of blood can be less.

As the priming volume of blood is decreased, burden imposed on a patient can also be mitigated. Consequently, by using bottom member 90A, heat-exchanger-integrated oxygenator 1 achieving further improved performance can be obtained.

It is noted that bottom member 90A does not have to have protrusion 95 in bottom member 90 described above. As bottom member 90A has raised bottom portion 96a, raised bottom portion 96b, and groove portion 96c as described above, such an effect as ability to make a priming volume of blood smaller can be obtained.

(Bottom Member 90B)

Figure 8:
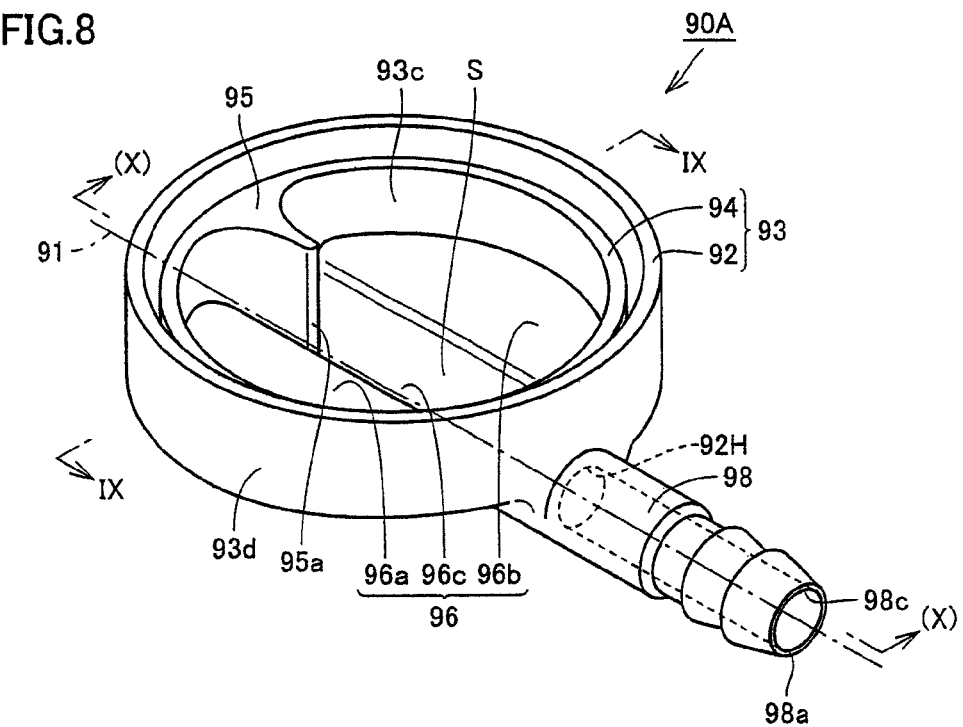
FIG. 8 is a perspective view showing a first variation of the bottom member used in the heat-exchanger-integrated oxygenator in the embodiment.
Figure 9:
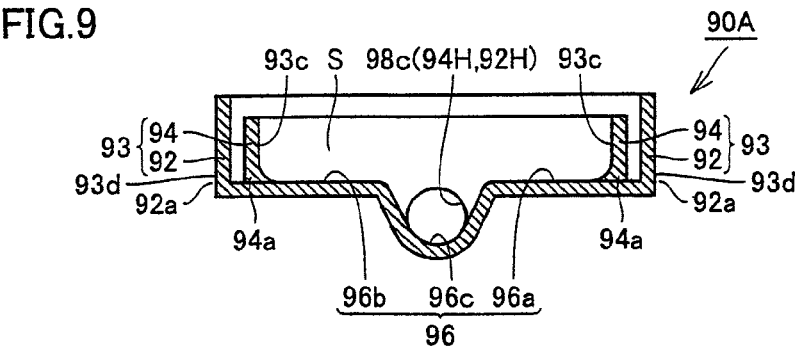
FIG. 9 is a cross-sectional view along the line IX-IX in FIG. 8, when viewed in a direction of an arrow.
Figure 10:
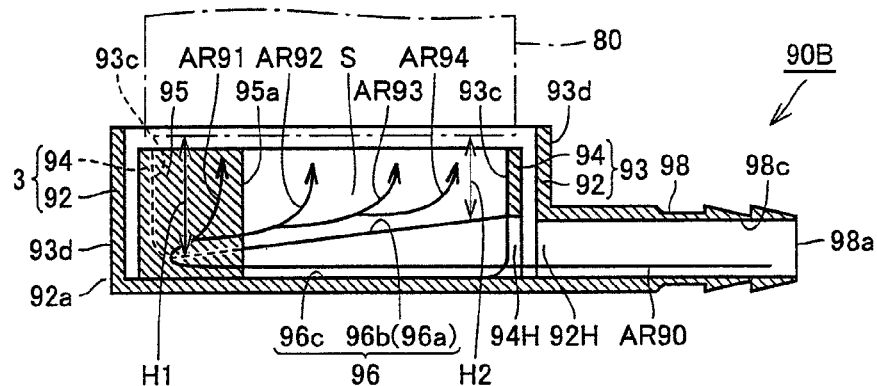
FIG. 10 is a cross-sectional view showing a second variation of the bottom member used in the heat-exchanger-integrated oxygenator in the embodiment.

FIG. 10 corresponds to a cross-sectional view along the line X-X in FIG. 8 when viewed in a direction of an arrow. A bottom member 90B (a second variation of bottom member 90) that can be used in heat-exchanger-integrated oxygenator 1 will be described with reference to FIG. 10. Only a difference from bottom member 90A described above will be described here.

In bottom member 90B, raised bottom portion 96a and raised bottom portion 96b are inclined. Specifically, on the side where blood inlet port 98 is provided, a distance H2 is defined between raised bottom portion 96a, raised bottom portion 96b and one end 8a of heat transfer pipe 8. On the other hand, on a side opposite to the side where blood inlet port 98 is provided, a distance H1 is defined between raised bottom portion 96a, raised bottom portion 96b and one end 8a of heat transfer pipe 8. Raised bottom portion 96a and raised bottom portion 96b are inclined such that distance H2 is smaller than distance H1.

According to bottom member 90B, the following effect in addition to the effects obtained by bottom member 90 described above and bottom member 90A described above can be obtained. The blood supplied from the one end 98a side of blood inlet port 98 to bottom member 90B reaches space S. As shown with an arrow AR90, the blood is gradually deflected toward the upper portion of the sheet surface (and in a vertical direction over the sheet surface) by protrusion 95. As shown with an arrow AR91 to an arrow AR94, the blood flows over each surface of raised bottom portion 96a and raised bottom portion 96b. Here, from a point of view of improvement in thermal efficiency of heat transfer pipe 8, the blood desirably flows at an equal flow rate in a direction shown with arrow AR91 to arrow AR94.

If it is assumed here that raised bottom portion 96a and raised bottom portion 96b are not inclined, a larger amount of blood flows to an arrow AR91 side. A distance until the blood reaches the arrow AR91 side after deflection of the blood is shorter than a distance until the blood reaches an arrow AR94 side, because the blood on the arrow AR91 side is higher in pressure than the blood on the arrow AR94 side.

According to bottom member 90B, raised bottom portion 96a and raised bottom portion 96b are inclined such that space S is wider on the arrow AR91 side and narrower on the arrow AR94 side. This inclination will generate an upward component (upward over the sheet surface) in the flow of blood toward the arrow AR94 side. Therefore, flow of the blood in a larger amount to the arrow AR91 side can be suppressed. According to bottom member 90B, the blood can flow into the plurality of heat transfer pipes 8 in distribution closer to equal. Consequently, by employing bottom member 90B, heat-exchanger-integrated oxygenator 1 achieving further improved performance can be obtained.

It is noted that bottom member 90B does not have to have protrusion 95 in bottom member 90 described above. As bottom member 90B has raised bottom portion 96a, raised bottom portion 96b, and groove portion 96c as described above, such an effect as ability to make a priming volume of blood smaller can be obtained.

(Bottom Member 90C)

Figure 11:
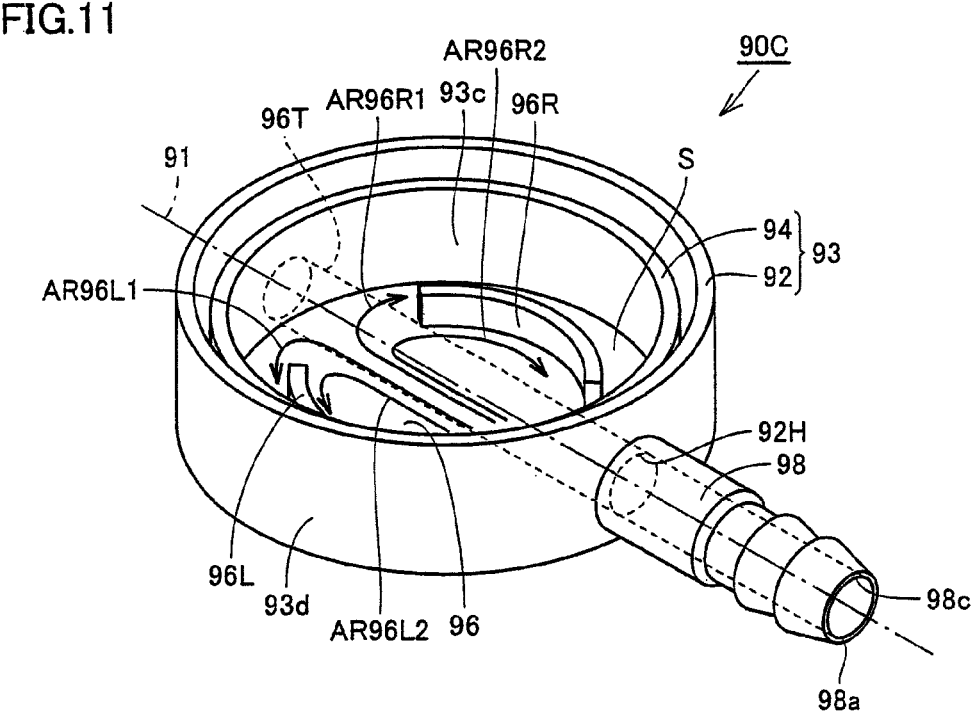
FIG. 11 is a perspective view showing a third variation of the bottom member used in the heat-exchanger-integrated oxygenator in the embodiment.

A bottom member 90C (a third variation of bottom member 90) that can be used in heat-exchanger-integrated oxygenator 1 will be described with reference to FIG. 11. Only a difference from bottom member 90 described above will be described here.

Bottom member 90C has annular wall 93, bottom surface 96, blood inlet port 98, a rib 96L, and a rib 96R. Bottom member 90C does not have protrusion 95 (see FIG. 5) in bottom member 90 described above.

Rib 96L and rib 96R are provided on bottom surface 96. Rib 96L and rib 96R are each formed in an arc shape bent along annular wall 93. Rib 96L and rib 96R stand on bottom surface 96, at a position not including a projection region 96T obtained by projecting inside 98c of blood inlet port 98 in direction of normal 91.

According to bottom member 90C, the following effect can be obtained. After the blood supplied from the one end 98a side of blood inlet port 98 to bottom member 90C reaches space S, it comes in contact with opposing inner circumferential surfaces 93c without coming in contact with rib 96L and rib 96R. After the blood is deflected, it is divided into blood that flows along inner circumferential surface 93c as shown with arrows AR96L1, AR96R1 and blood that flows along respective inner sides of rib 96L and rib 96R as shown with arrows AR96L2, AR96R2. The blood flows through the inside of space S toward blood inlet port 98. After the inside of space S is filled with the blood, the blood flows into the inside of heat transfer pipe 8 from one end 8a of heat transfer pipe 8 in pipe group 80.

If it is assumed here that bottom member 90C does not have rib 96L and rib 96R, most of the blood supplied through blood inlet port 98 flows on the outer circumferential side of bottom surface 96 along opposing inner circumferential surfaces 93c. An amount of the blood that flows in space S is greater on the outer circumferential side of bottom surface 96 and smaller on the inner circumferential side of bottom surface 96. In the inside of space S, the blood on the outer circumferential side is higher in pressure than the blood on the inner circumferential side. The blood flows in a greater amount into heat transfer pipe 8 arranged on the outer circumferential side and flows in a smaller amount into heat transfer pipe 8 arranged on the inner circumferential side. An amount of blood that flows in heat transfer pipe 8 becomes unequal and efficiency in heat exchange by heat transfer pipe 8 lowers.

According to bottom member 90C, as rib 96L and rib 96R are provided, the blood is split into blood that flows along inner circumferential surface 93c and blood that flows along the inner sides of rib 96L and rib 96R. Inequality in amount of blood that flows in heat transfer pipe 8 can be suppressed and lowering in efficiency in heat exchange by heat transfer pipe 8 can be suppressed. Consequently, by employing bottom member 90C, heat-exchanger-integrated oxygenator 1 achieving further improved performance can be obtained.

It is noted that bottom member 90C does not have to have protrusion 95 in bottom member 90 described above. As bottom member 90C has rib 96L and rib 96R as described above, such an effect as ability to suppress inequality in amount of blood that flows in heat transfer pipe 8 can be obtained.

(Bottom Member 90D)

Figure 12:
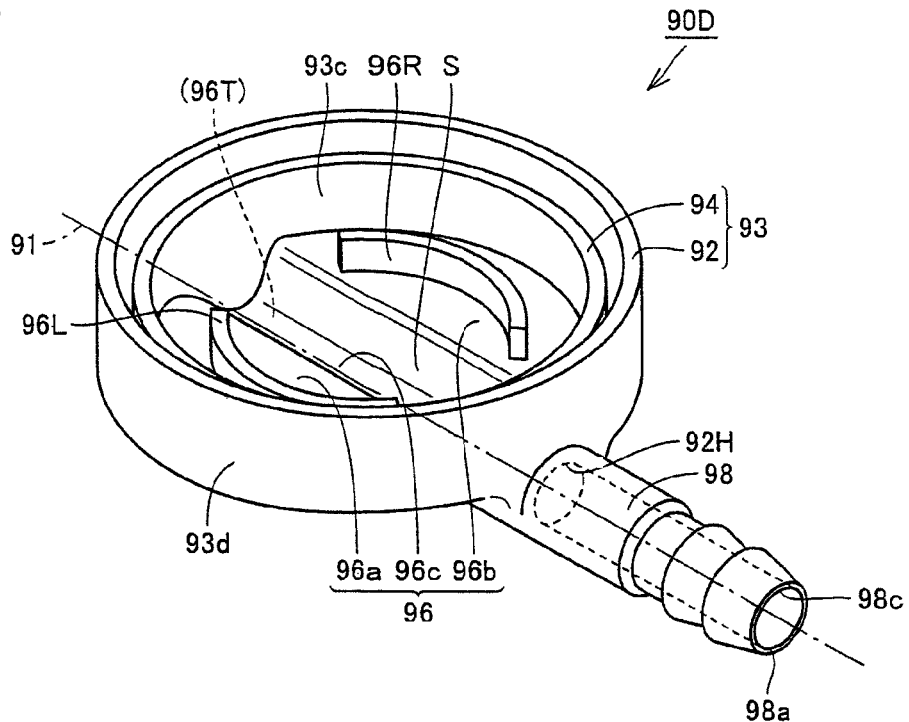
FIG. 12 is a perspective view showing a fourth variation of the bottom member used in the heat-exchanger-integrated oxygenator in the embodiment.

A bottom member 90D (a fourth variation of bottom member 90) that can be used in heat-exchanger-integrated oxygenator 1 will be described with reference to FIG. 12. Only a difference from bottom member 90C will be described here. In bottom member 90D, as in bottom member 90A described above, raised bottom portion 96a, raised bottom portion 96b, and groove portion 96c are provided in bottom surface 96. Rib 96L is disposed on the surface of raised bottom portion 96a. Rib 96R is disposed on the surface of raised bottom portion 96b.

According to bottom member 90D, the following effect in addition to the effects obtained by bottom member 90C described above can be obtained. According to bottom member 90D, the blood that flows through groove portion 96c and the blood that flows over each surface of raised bottom portion 96a and raised bottom portion 96b flow through portions displaced in a direction of height and hence a chance of contact with each other is less. Occurrence of a turbulent flow and pressure loss in the blood can be suppressed. In addition, since raised bottom portion 96a, raised bottom portion 96b, and groove portion 96c are provided in bottom surface 96, a priming volume of blood can be made smaller. Consequently, by employing bottom member 90D, heat-exchanger-integrated oxygenator 1 achieving further improved performance can be obtained.

(Bottom Member 90E)

Figure 13:
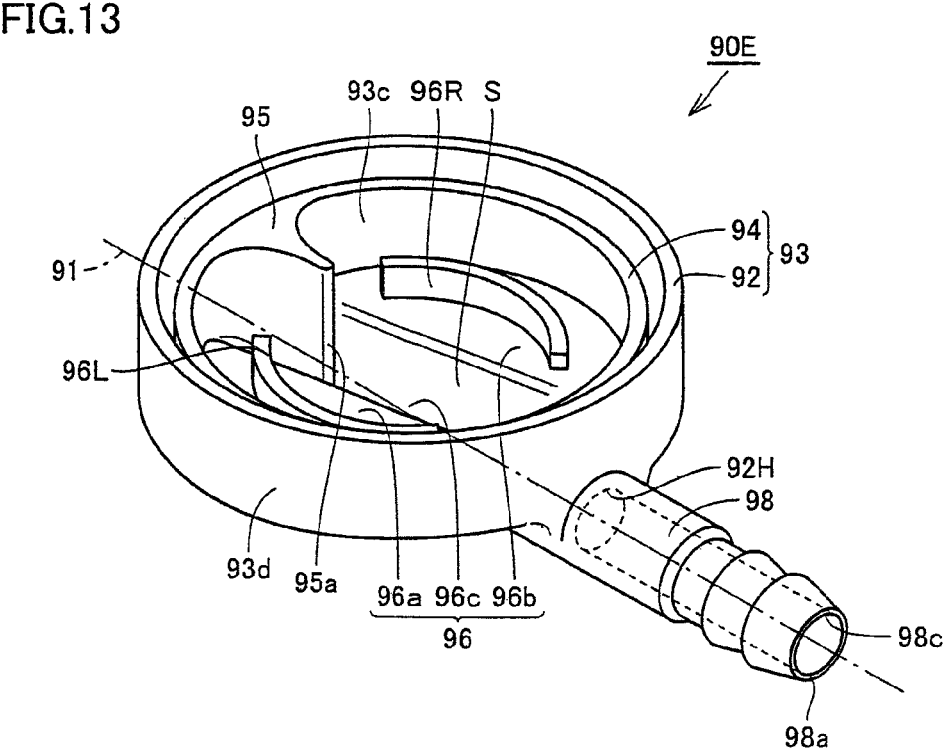
FIG. 13 is a perspective view showing a fifth variation of the bottom member used in the heat-exchanger-integrated oxygenator in the embodiment.

A bottom member 90E (a fifth variation of bottom member 90) that can be used in heat-exchanger-integrated oxygenator 1 will be described with reference to FIG. 13. Bottom member 90E has rib 96L and rib 96R as in bottom member 90C, in addition to the features of bottom member 90B described above.

Specifically, in bottom member 90E, raised bottom portion 96a, raised bottom portion 96b, and groove portion 96c are provided in bottom surface 96. Raised bottom portion 96a and raised bottom portion 96b are inclined as in bottom member 90B described above. Rib 96L is disposed on the surface of raised bottom portion 96a. Rib 96R is disposed on the surface of raised bottom portion 96b.

According to bottom member 90E, an effect the same as in bottom member 90C in addition to the effects as in bottom member 90B described above can be obtained. Consequently, by employing bottom member 90E, heat-exchanger-integrated oxygenator 1 achieving further improved performance can be obtained.

(Heat Exchanger Case 70 and Pipe Group 80)

Figure 14:
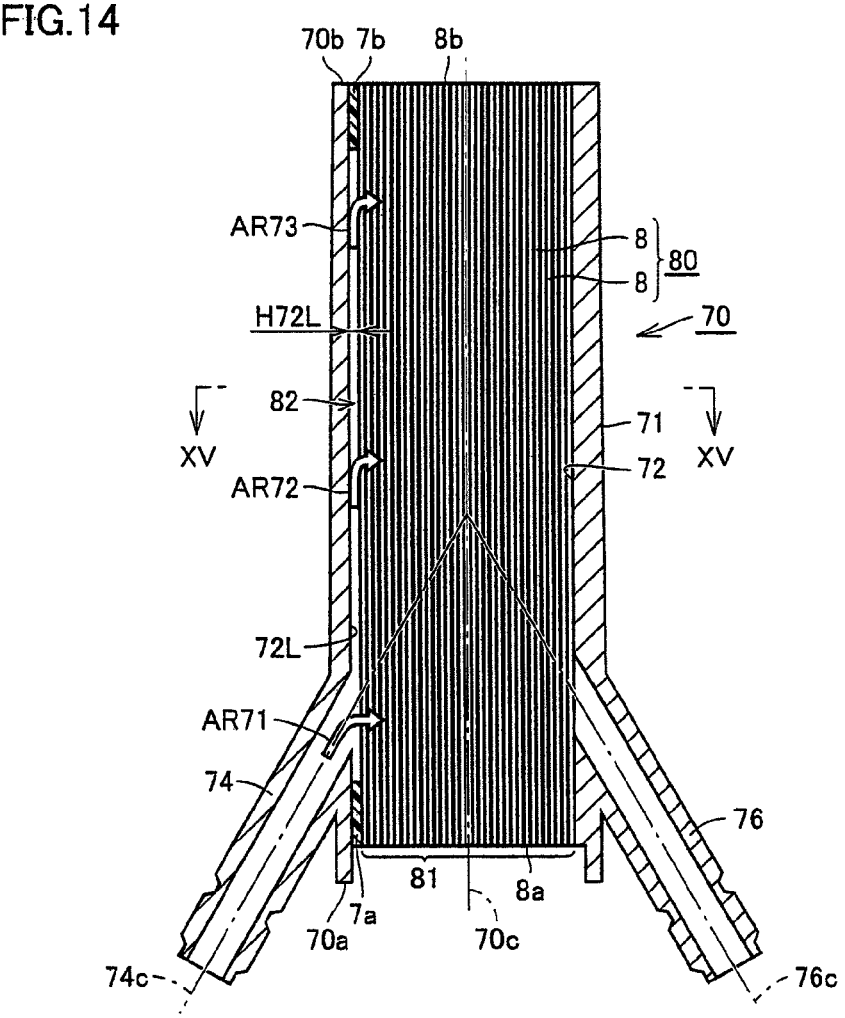
FIG. 14 is a cross-sectional view showing a heat exchanger case and a pipe group used in the heat-exchanger-integrated oxygenator in the embodiment.
Figure 15:
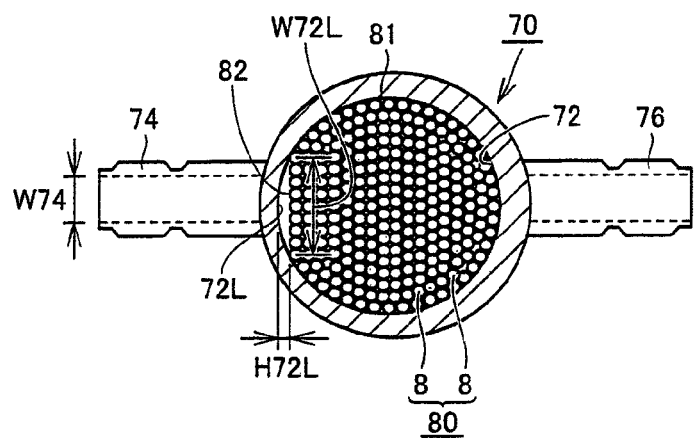
FIG. 15 is a cross-sectional view along the line XV-XV in FIG. 14, when viewed in a direction of an arrow.

Heat exchanger case 70 and pipe group 80 used in heat-exchanger-integrated oxygenator 1 will be described with reference to FIGS. 14 and 15. Referring initially to FIG. 14, as described above, the plurality of heat transfer pipes 8 are loaded as pipe group 80 in the inside of heat exchanger case 70. Heat exchange medium inlet port 74 and heat exchange medium outlet port 76 are attached to outer surface 71 on the one end 70a side of heat exchanger case 70.

Heat exchange medium inlet port 74 has a shape of a straight pipe. Heat exchange medium inlet port 74 is attached such that an extension of a pipe axis 74c crosses central cylinder axis 70c of heat exchanger case 70. Heat exchange medium inlet port 74 is attached such that the extension of pipe axis 74c is directed toward the other end 8b of heat transfer pipe 8. Heat exchange medium inlet port 74 supplies a prescribed heat exchange medium to the outer surface of heat transfer pipe 8.

Heat exchange medium inlet port 74 and heat exchange medium outlet port 76 are located on respective opposing sides in a direction of cylinder diameter of heat exchanger case 70. Heat exchange medium outlet port 76 discharges the heat exchange medium supplied to the outer surface of heat transfer pipe 8 to the outside of heat exchanger case 70.

Heat exchange medium outlet port 76 may have a shape of a straight pipe similarly to heat exchange medium inlet port 74. Heat exchange medium outlet port 76 may be attached such that an extension of a pipe axis 76c crosses central cylinder axis 70c of heat exchanger case 70. Heat exchange medium outlet port 76 may be attached such that the extension of pipe axis 76c is directed toward the other end 8b of heat transfer pipe 8.

The plurality of heat transfer pipes 8 are loaded as pipe group 80 in the inside of heat exchanger case 70 along the direction of cylinder axis of heat exchanger case 70 while they are bundled in a substantially columnar shape. Blood flows through bottom member 90 from one end 8a of heat transfer pipe 8 to the inside of heat transfer pipe 8.

The plurality of heat transfer pipes 8 have a circumferential portion 81 and a first chord 82 in a bundled state. Circumferential portion 81 refers to a portion arranged at a short distance from inner surface 72 of heat exchanger case 70 when the plurality of heat transfer pipes 8 (pipe group 80) are loaded in the inside of heat exchanger case 70, of the plurality of heat transfer pipes 8 in a bundled state. A short distance herein means, for example, a distance from approximately 0.1 mm to approximately 2.0 mm. Approximately 0.1 mm to approximately 2.0 mm herein means, for example, approximately 2.0 mm at the maximum, although there is a difference depending on arrangement of heat transfer pipes 8. First chord 82 is a portion that retracts by a distance H72L toward the center in the direction of cylinder diameter from an arc formed by circumferential portion 81, of the plurality of heat transfer pipes 8 in the bundled state. Distance H72L is, for example, from approximately 4.0 mm to approximately 5.0 mm.

First chord 82 extends from the one end 8a side of heat transfer pipe 8 to the other end 8b side of heat transfer pipe 8. Referring to FIG. 15, first chord 82 has a prescribed width W72L. Width W72L is desirably set to be greater than a pipe diameter W74 of heat exchange medium inlet port 74.

The plurality of heat transfer pipes 8 in the bundled state are loaded in the inside of heat exchanger case 70 such that first chord 82 and inner surface 72 (72L) of heat exchanger case 70 on the side where heat exchange medium inlet port 74 is attached are opposed to each other. Referring to FIG. 14, opposing ends of first chord 82 are closed by a sealing member 7a and a sealing member 7b, respectively.

(Function and Effect)

Referring to FIG. 14, as described above, a heat exchange medium (such as water) at a prescribed temperature is supplied through heat exchange medium inlet port 74 to heat exchanger case 70. As shown with an arrow AR71, the heat exchange medium that has flowed through the inside of heat exchange medium inlet port 74 reaches the inside of heat exchanger case 70. As shown with arrow AR71 to an arrow AR73, the heat exchange medium spreads (is distributed) in the direction of cylinder axis (the up/down direction over the sheet surface) between first chord 82 and inner surface 72 (72L) of heat exchanger case 70 on the side where heat exchange medium inlet port 74 is attached. The heat exchange medium comes in contact with the entire outer surface of heat transfer pipe 8 in pipe group 80.

If it is assumed that the plurality of heat transfer pipes 8 in the bundled state do not have first chord 82, heat transfer pipe 8 and inner surface 72 (72L) of heat exchanger case 70 on the side where heat exchange medium inlet port 74 is attached come in intimate contact with each other. Most of the heat exchange medium supplied through heat exchange medium inlet port 74 comes in contact only with the one end 8a side of heat transfer pipe 8, without spreading in the direction of cylinder axis. After most of the heat exchange medium flows only over the outer surface on the one end 8a side of heat transfer pipe 8, it is discharged to the outside of heat exchanger case 70 through heat exchange medium outlet port 76. An area of contact between the heat exchange medium and the outer surface of heat transfer pipe 8 in pipe group 80 decreases and efficiency in heat exchange lowers.

As the plurality of heat transfer pipes 8 in the bundled state have first chord 82, in first chord 82, the heat exchange medium can come in contact with the entire outer surface of heat transfer pipe 8 in pipe group 80. Since an area of contact between the heat exchange medium and the outer surface of heat transfer pipe 8 in pipe group 80 increases, efficiency in heat exchange can be improved. Consequently, by employing heat exchanger case 70 and pipe group 80 as described above, heat-exchanger-integrated oxygenator 1 achieving further improved performance can be obtained.

In order to allow the heat exchange medium to further be in contact with the entire outer surface of heat transfer pipe 8 in pipe group 80, prescribed distance H72L with respect to first chord 82 is desirably optimized. Distance H72L is optimized in accordance with a size of heat exchanger case 70, a flow rate of blood, pipe diameter W74 of heat exchange medium inlet port 74, or the like.

(Heat Exchanger Case 70A and Pipe Group 80)

Figure 16:
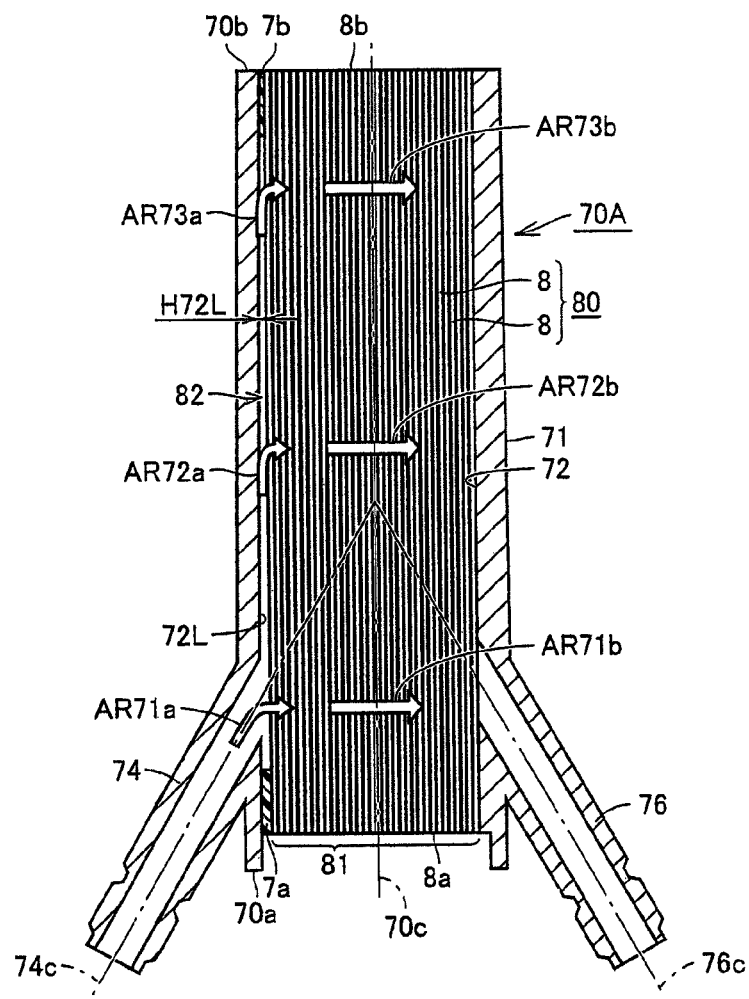
FIG. 16 is a cross-sectional view showing a first variation of the heat exchanger case used in the heat-exchanger-integrated oxygenator in the embodiment and the pipe group used in the heat-exchanger-integrated oxygenator in the embodiment.

A heat exchanger case 70A (a first variation of heat exchanger case 70) that can be used in heat-exchanger-integrated oxygenator 1 and pipe group 80 will be described with reference to FIG. 16. Only a difference from heat exchanger case 70 will be described here. Since pipe group 80 is the same as described above, description thereof will not be repeated.

In heat exchanger case 70A, inner surface 72L of heat exchanger case 70A on the side where heat exchange medium inlet port 74 is attached is formed substantially in such a tapered shape as gradually protruding toward the center in the direction of cylinder diameter. With regard to inner surface 72L formed substantially in the tapered shape, distance H72L between inner surface 72L and first chord 82 becomes gradually smaller from the one end 70a side of heat exchanger case 70A toward the other end 70b of heat exchanger case 70A. In other words, distance H72L between inner surface 72L and first chord 82 is greater on the one end 70a side of heat exchanger case 70A and smaller on the other end 70b side of heat exchanger case 70A.

According to heat exchanger case 70A and pipe group 80, the following effect in addition to the effects obtained by heat exchanger case 70A described above can be obtained. As shown with an arrow AR71a to an arrow AR73a, the heat exchange medium supplied through heat exchange medium inlet port 74 spreads (is distributed) in the direction of cylinder axis (the up/down direction over the sheet surface) between first chord 82 and inner surface 72 (72L) of heat exchanger case 70 on the side where heat exchange medium inlet port 74 is attached.

Inner surface 72L is formed to incline in a tapered shape such that distance H72L in the direction of cylinder diameter between inner surface 72 (72L) of heat exchanger case 70A on the side where heat exchange medium inlet port 74 is attached and first chord 82 is smaller on an arrow AR73a side than on an arrow AR71a side. This inclination will produce a component in a direction substantially orthogonal to heat transfer pipe 8 (a left/right direction over the sheet surface) toward the arrow AR73a side, in the flow of the heat exchange medium.

Therefore, as shown with an arrow AR73b, the heat exchange medium that flows toward the arrow AR73a side flows over the outer surface of heat transfer pipe 8 in a direction substantially orthogonal to heat transfer pipe 8 (the left/right direction over the sheet surface). Similarly, the heat exchange medium that flows toward the arrow AR71a and arrow AR72a side also flows over the outer surface of heat transfer pipe 8 in a direction substantially orthogonal to heat transfer pipe 8, as shown with an arrow AR71b and an arrow AR72b. Since the heat exchange medium flows substantially orthogonal to the entire heat transfer pipe 8, high efficiency in heat exchange can be obtained.

In order for the heat exchange medium to flow in a direction closer to orthogonal to the entire heat transfer pipe 8 and in order for the heat exchange medium to more uniformly flow over the entire heat transfer pipe 8, a tapered shape of inner surface 72L of heat exchanger case 70A, width W72L of first chord 82 in pipe group 80, and the like are desirably optimized in accordance with a size of heat exchanger case 70A, a flow rate of blood, pipe diameter W74 of heat exchange medium inlet port 74, or the like.

In general, in a case where a heat transfer pipe is made use of as a heat exchanger, from a point of view of efficiency in heat exchange, a direction of flow of a medium of which heat is to be exchanged (such as blood) in the inside of the heat transfer pipe is desirably reverse (counterflow) or orthogonal (orthogonal flow) to a direction of flow of the heat exchange medium over the outer surface of the heat transfer pipe.

In a general heat exchanger case, in consideration of user's convenience, similarly to heat exchanger case 70A, a heat exchange medium inlet port (74) and a heat exchange medium outlet port (76) are attached to a one end side of a heat exchanger case. In order to obtain a counterflow above in such a general heat exchanger case, a prescribed separate part for guiding the heat exchange medium supplied to the heat exchanger case to the other end side of the heat exchanger case (the other end 70b side in heat exchanger case 70A) is required. The separate part is provided in the inside or on the outer surface of the heat exchanger case. Provision of a separate part causes increase in volume or increase in manufacturing cost of the heat exchanger case.

According to heat exchanger case 70A and pipe group 80, inner surface 72L is formed substantially in a tapered shape and hence an orthogonal flow can readily be obtained without providing a separate part. According to heat exchanger case 70A and pipe group 80, efficiency in heat exchange equal to or higher than that of the counterflow above can readily be obtained. Consequently, by employing heat exchanger case 70A and pipe group 80, heat-exchanger-integrated oxygenator 1 achieving further improved performance can be obtained.

(Heat Exchanger Case 70A and Pipe Group 80A)

Heat exchanger case 70A and a pipe group 80A (a variation of pipe group 80) that can be used in heat-exchanger-integrated oxygenator 1 will be described with reference to FIGS. 17 and 18. Since heat exchanger case 70A is the same as described above, description thereof will not be repeated. Only a difference from pipe group 80 will be described here.

Figure 17:
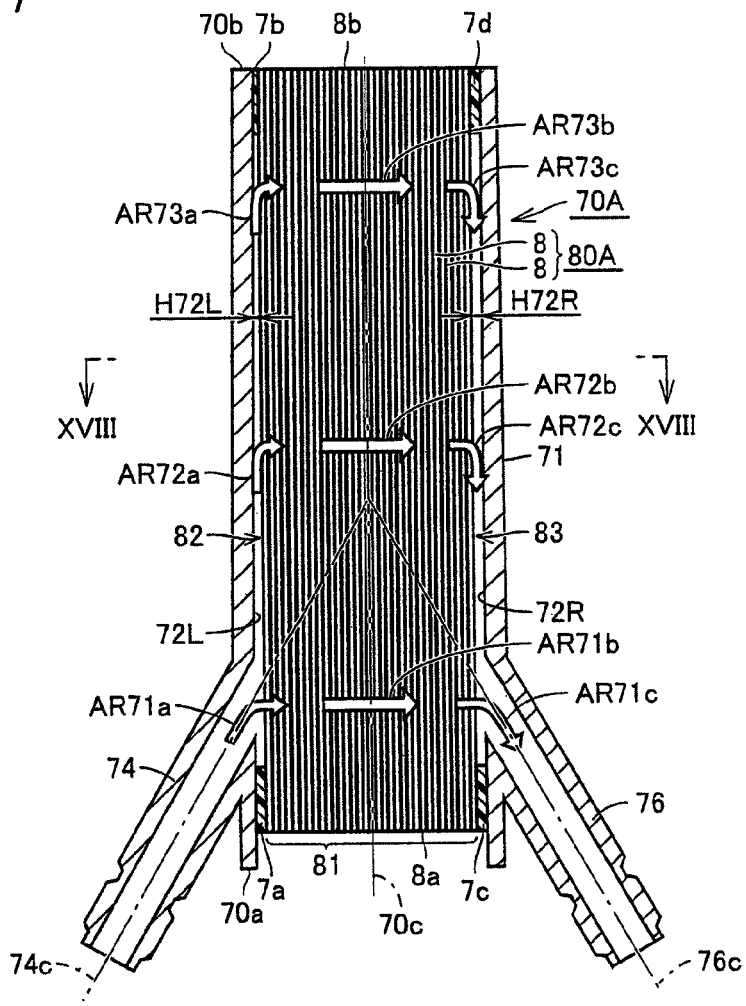
FIG. 17 is a cross-sectional view showing the first variation of the heat exchanger case used in the heat-exchanger-integrated oxygenator in the embodiment and a variation of the pipe group used in the heat-exchanger-integrated oxygenator in the embodiment.
Figure 18:
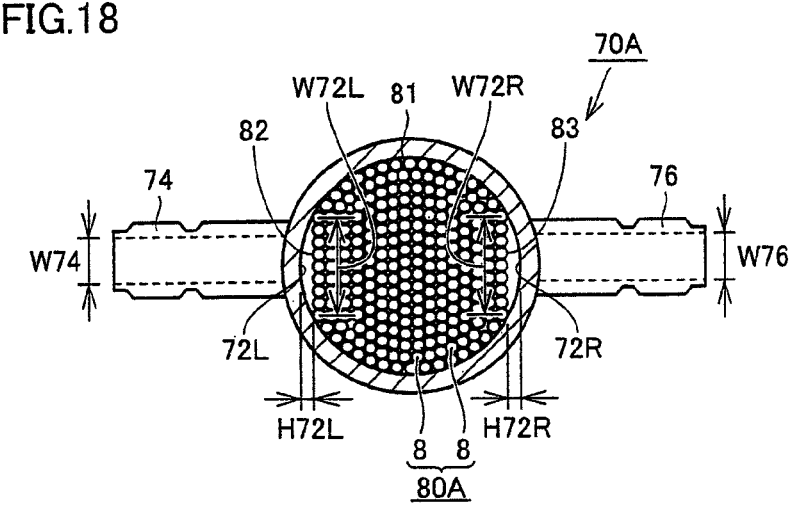
FIG. 18 is a cross-sectional view along the line XVIII-XVIII in FIG. 17, when viewed in a direction of an arrow.

Referring mainly to FIG. 17, in pipe group 80A, the plurality of heat transfer pipes 8 further have a second chord 83. Second chord 83 is a portion that retracts by a distance H72R toward the center in the direction of cylinder diameter from an arc formed by circumferential portion 81, of the plurality of heat transfer pipes 8 in the bundled state. Second chord 83 is located on the side opposite in the direction of cylinder diameter to first chord 82.

Second chord 83 extends from the one end 8a side of heat transfer pipe 8 toward the other end 8b of heat transfer pipe 8. Referring to FIG. 18, second chord 83 has a prescribed width W72R. Width W72R is desirably set to be greater than a pipe diameter W76 of heat exchange medium outlet port 76.

As described above, the plurality of heat transfer pipes 8 in the bundled state are loaded in the inside of heat exchanger case 70 such that first chord 82 and inner surface 72 (72L) of heat exchanger case 70 on the side where heat exchange medium inlet port 74 is attached are opposed to each other. Thus, second chord 83 and inner surface 72 (72R) of heat exchanger case 70 on the side where heat exchange medium outlet port 76 is attached are opposed to each other. Referring to FIG. 17, opposing ends of second chord 83 are closed by a sealing member 7c and a sealing member 7d, respectively.

According to heat exchanger case 70A and pipe group 80A, the following effect in addition to the effects obtained by heat exchanger case 70A and pipe group 80 described above can be obtained. The heat exchange medium supplied through heat exchange medium inlet port 74 to heat exchanger case 70A spreads (is distributed) in the direction of cylinder axis (the up/down direction over the sheet surface) between first chord 82 and inner surface 72 (72L) of heat exchanger case 70A on the side where heat exchange medium inlet port 74 is attached. The heat exchange medium comes in contact with the entire outer surface of heat transfer pipe 8 in pipe group 80.

After the heat exchange medium flows over the outer surface of heat transfer pipe 8, it flows in between second chord 83 and inner surface 72 (72R) of heat exchanger case 70A where heat exchange medium outlet port 76 is attached, as shown with an arrow AR71c to an arrow AR73c.

As the plurality of heat transfer pipes 8 in the bundled state have second chord 83, the heat exchange medium that flows over the outer surface of heat transfer pipe 8 in a direction shown with arrow AR71b to arrow AR73b can flow over the outer surface of heat transfer pipe 8 in a direction closer to orthogonal to heat transfer pipe 8 (than heat exchanger case 70A and pipe group 80).

According to heat exchanger case 70A and pipe group 80A, further higher efficiency in heat exchange can be obtained. Consequently, by employing heat exchanger case 70A and pipe group 80A, heat-exchanger-integrated oxygenator 1 achieving further improved performance can be obtained. Though an embodiment where heat exchanger case 70A and pipe group 80A are combined with each other has been described above, heat exchanger case 70 described above may be combined with pipe group 80A. Specifically, heat exchanger case 70 in which inner surface 72L is not formed in such a substantially tapered shape as gradually protruding toward the center in the direction of cylinder diameter may be combined with pipe group 80A having first chord 82 and second chord 83.

(Heat Exchanger Case 70B and Pipe Group 80A)

Figure 19:
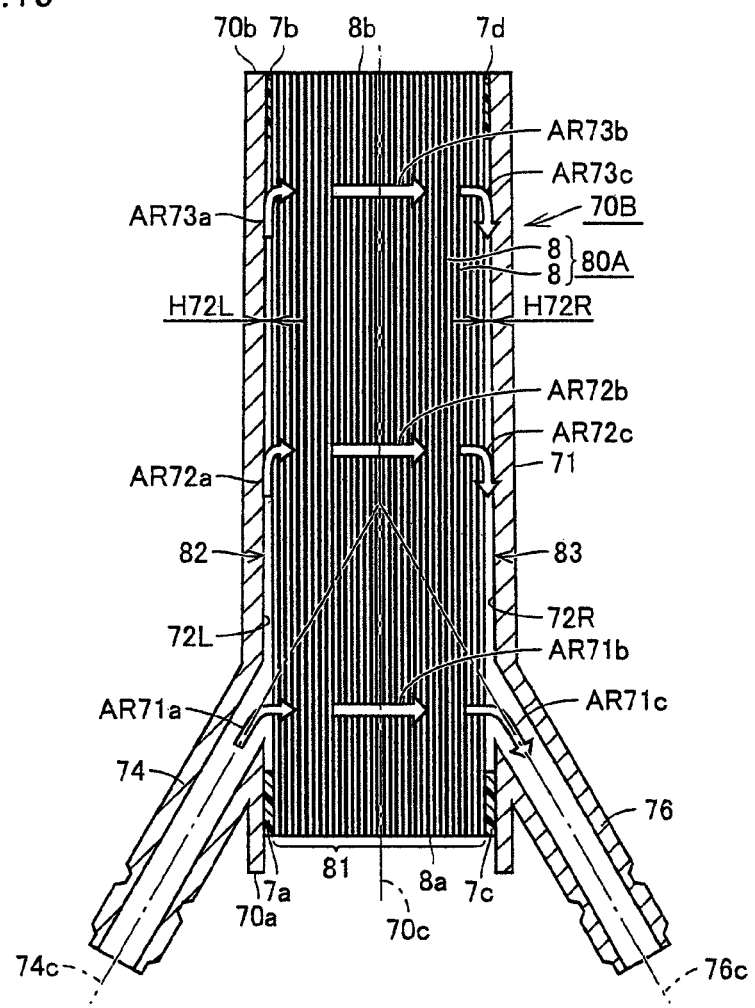
FIG. 19 is a cross-sectional view showing a second variation of the heat exchanger case used in the heat-exchanger-integrated oxygenator in the embodiment and the variation of the pipe group used in the heat-exchanger-integrated oxygenator in the embodiment.

A heat exchanger case 70B (a second variation of heat exchanger case 70) that can be used in heat-exchanger-integrated oxygenator 1 and pipe group 80A will be described with reference to FIG. 19. Only a difference from heat exchanger case 70A will be described here. Since pipe group 80A is the same as described above, description thereof will not be repeated.

In heat exchanger case 70B, inner surface 72R of heat exchanger case 70B on the side where heat exchange medium outlet port 76 is attached is formed substantially in such a tapered shape as gradually protruding toward the center in the direction of cylinder diameter. With regard to inner surface 72R formed substantially in the tapered shape, distance H72R between inner surface 72R and second chord 83 becomes gradually smaller from the one end 70a side of heat exchanger case 70 toward the other end 70b of heat exchanger case 70. In other words, distance H72R between inner surface 72R and second chord 83 is greater on the one end 70a side of heat exchanger case 70B and smaller on the other end 70b side of heat exchanger case 70B.

According to heat exchanger case 70B and pipe group 80A, effects similar to those obtained by heat exchanger case 70A and pipe group 80A described above can be obtained.

In order for the heat exchange medium to flow in a direction closer to orthogonal to the entire heat transfer pipe 8 and in order for the heat exchange medium to more uniformly flow over the entire heat transfer pipe 8, a tapered shape of inner surface 72R of heat exchanger case 70B, width W72R of second chord 83 in pipe group 80A, and the like are desirably optimized in accordance with a size of heat exchanger case 70B, a flow rate of blood, pipe diameter W76 of heat exchange medium outlet port 76, or the like.

Heat exchanger case 70B and pipe group 80A may be constructed symmetrically, with central cylinder axis 70c of heat exchanger case 70B lying therebetween. According to such a construction, since it is not necessary to distinguish between an inlet and an outlet at the time of connection of a tube or the like, user's convenience can be improved.

(Cylindrical Core 40)

Cylindrical core 40 used in heat-exchanger-integrated oxygenator 1 will be described with reference to FIGS. 20 and 21. Though FIG. 21 shows outer surface 41 of cylindrical core 40 and bundle 30 slightly distant from each other for the sake of convenience of illustration, they are actually in intimate contact with each other.

Figure 20:
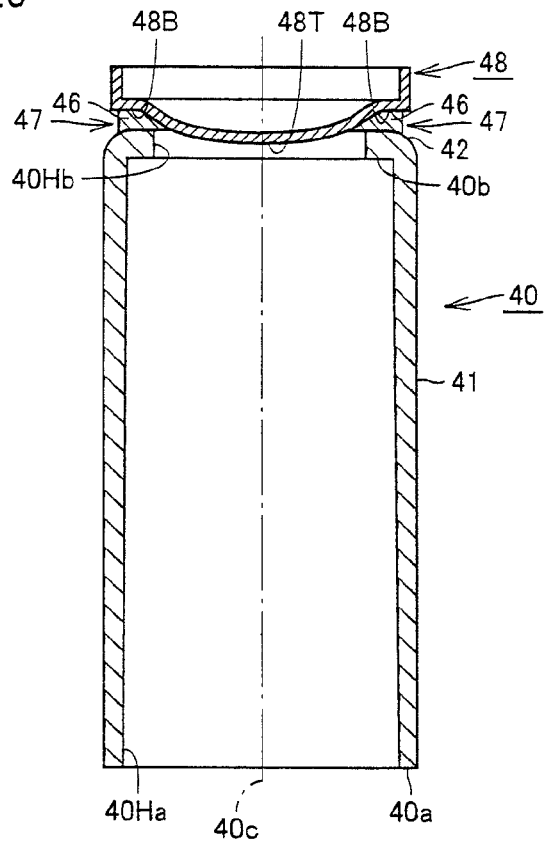
FIG. 20 is a cross-sectional view showing a cylindrical core used in the heat-exchanger-integrated oxygenator in the embodiment.
Figure 21:
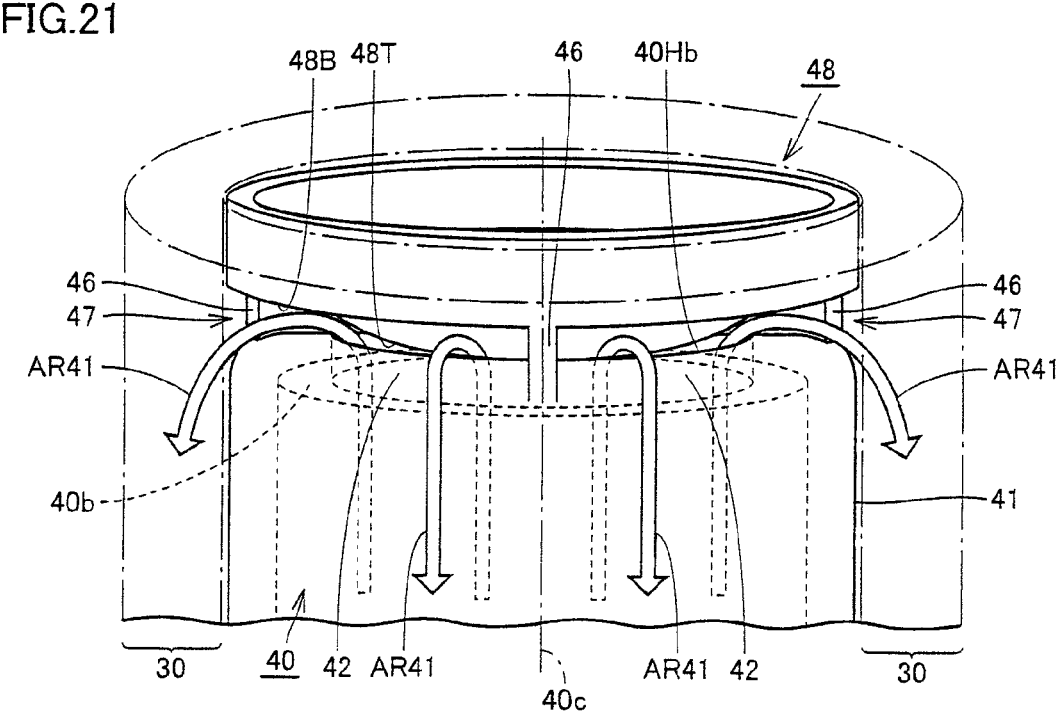
FIG. 21 is an enlarged perspective view showing a part (on the other end side) of the cylindrical core used in the heat-exchanger-integrated oxygenator in the embodiment.

Referring mainly to FIG. 20, as described above, cylindrical core 40 is formed in a cylindrical shape. Cylindrical core 40 has a circular opening 40Ha on the one end 40a side and a circular opening 40Hb on the other end 40b side. A diameter of opening 40Hb is set to be smaller than a diameter of opening 40Ha.

An elbow portion 42 extending inward in the direction of cylinder diameter toward opening 40Hb is provided on outer surface 41 on the other end 40b side of cylindrical core 40. On a surface of elbow portion 42, a plurality of thin-plate-shaped support ribs 46 extending in a direction in parallel to cylinder axis 40c (the up/down direction over the sheet surface) are provided. Support ribs 46 connect diffusion portion 48 and the surface of elbow portion 42 to each other.

Diffusion portion 48 has protruding portion 48T and a base portion 48B. Base portion 48B is formed substantially in a columnar shape. Protruding portion 48T is formed substantially in a shape of a cone protruding from a surface of a central portion (on the lower side of the sheet surface) of base portion 48B toward opening 40Hb in cylindrical core 40. A portion around the central portion of protruding portion 48T desirably forms a gently convex surface (see FIG. 20).

Outer surface 41 on the other end 40b side of cylindrical core 40 (a surface of elbow portion 42 in cylindrical core 40) is subjected to round chamfering around the entire circumference of elbow portion 42. In other words, the construction is such that an outer diameter of elbow portion 42 gradually decreases from one end 40a of cylindrical core 40 toward the other end 40b of cylindrical core 40.

(Function and Effect)

Referring to FIG. 21, as described above, blood that has reached the other end 8b of heat transfer pipe 8 (see FIG. 4) flows out toward protruding portion 48T of diffusion portion 48. After the blood comes in contact with protruding portion 48T, it changes a direction of flow so as to move outward in the direction of cylinder diameter.

The blood is discharged through outlet portion 47 surrounded by elbow portion 42, base portion 48B, and support ribs 46 and the blood comes in contact with the outer surface of the hollow fiber membrane in bundle 30. Some of the blood comes in contact with the outer surface of the hollow fiber membrane while forming a gentle arc along outer surface 41 of elbow portion 42, as shown with an arrow AR41. The blood flows through a gap formed between the hollow fiber membranes.

If it is assumed that round chamfering in elbow portion 42 is not performed, the entire blood discharged through outlet portion 47 flows in a direction orthogonal to the outer surface of the hollow fiber membrane and comes in contact with the outer surface of the hollow fiber membrane from the front. Thus, pressure loss is caused in the blood. Cells and thrombocytes in some of the blood may be destructed.

According to cylindrical core 40, since round chamfering in elbow portion 42 is performed, the blood can gradually be deflected. Occurrence of pressure loss in the blood can be suppressed and destruction of cells and thrombocytes in the blood can also be suppressed. Consequently, by employing cylindrical core 40, heat-exchanger-integrated oxygenator 1 achieving further improved performance can be obtained.

(Cylindrical Core 40A)

Figure 22:
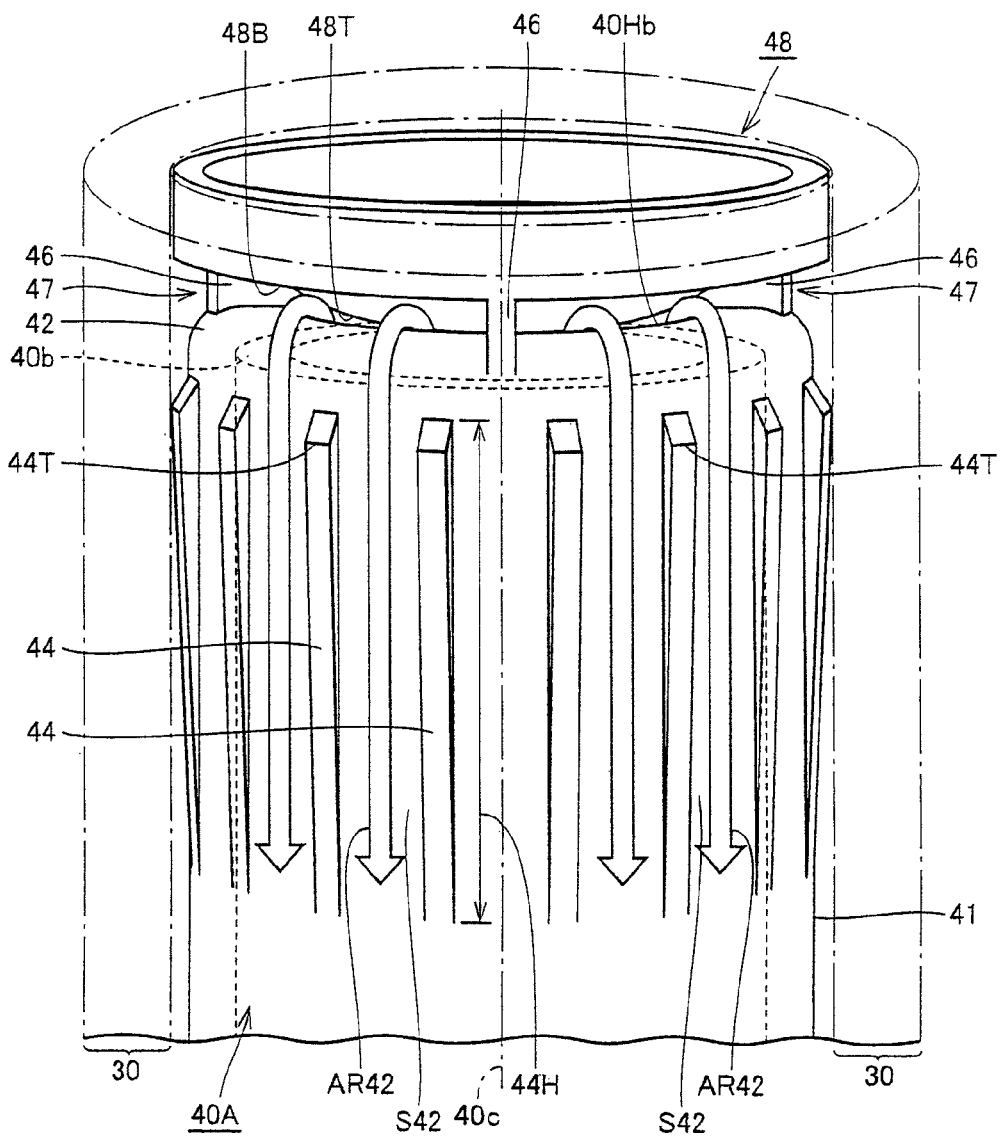
FIG. 22 is an enlarged perspective view showing a part (on the other end side) of a variation of the cylindrical core used in the heat-exchanger-integrated oxygenator in the embodiment.

A cylindrical core 40A (a variation of cylindrical core 40) that can be used in heat-exchanger-integrated oxygenator 1 will be described with reference to FIG. 22. Only a difference from cylindrical core 40 will be described here. Though FIG. 22 shows outer surface 41 of cylindrical core 40 and bundle 30 slightly distant from each other for the sake of convenience of illustration, they are actually in intimate contact with each other, except for a gap S42 which will be described later.

In cylindrical core 40A, a plurality of ribs 44 are provided on outer surface 41 on the other end 40b side. Ribs 44 protrude from outer surface 41 outward in the direction of cylinder diameter. A height of rib 44 is desirably set such that it becomes greater toward a top portion 44T from the other end 40b side to the one end 40a side and it gradually becomes smaller after it reaches top portion 44T.

Rib 44 extends in a direction substantially in parallel to cylinder axis 40c from the other end 40b side of cylindrical core 40. Rib 44 extends by a length 44H not reaching one end 40a of cylindrical core 40, with the other end 40b side of cylindrical core 40A being defined as the origin. Ribs 44 are aligned at a prescribed distance from each other in a circumferential direction.

Owing to ribs 44, gap S42 extending in a direction substantially in parallel to cylinder axis 40c is formed between outer surface 41 of cylindrical core 40 and the hollow fiber membrane in bundle 30. Gap S42 communicates with outlet portion 47. In cylindrical core 40A, as in cylindrical core 40 described above, round chamfering in elbow portion 42 may be performed.

(Function and Effect)

As described above, blood that has reached the other end 8b of heat transfer pipe 8 (see FIG. 4) flows out toward protruding portion 48T of diffusion portion 48. After the blood comes in contact with protruding portion 48T, it changes a direction of flow so as to move outward in the direction of cylinder diameter.

The blood is discharged through outlet portion 47 and it comes in contact with the outer surface of the hollow fiber membrane in bundle 30. Some of the blood gradually comes in contact with the outer surface of the hollow fiber membrane after it flows into gap S42, as shown with an arrow AR42. Thereafter, some of the blood flows through a gap formed between the hollow fiber membranes.

If it is assumed that ribs 44 are not provided on outer surface 41, the entire blood discharged through outlet portion 47 flows in a direction orthogonal to the outer surface of the hollow fiber membrane and comes in contact with the outer surface of the hollow fiber membrane from the front. Thus, pressure loss is caused in the blood. Cells and thrombocytes in some of the blood may be destructed.

According to cylindrical core 40A, since ribs 44 are provided on outer surface 41, the blood can gradually flow into the gap formed between the hollow fiber membranes. Occurrence of pressure loss in the blood can be suppressed and destruction of cells and thrombocytes in the blood can also be suppressed. Consequently, by employing cylindrical core 40A, heat-exchanger-integrated oxygenator 1 achieving further improved performance can be obtained.

Although the modes for carrying out the invention according to the present invention have been described, it should be understood that the embodiments disclosed herein are illustrative and non-restrictive in every respect. The scope of the present invention is defined by the terms of the claims and is intended to include any modifications within the scope and meaning equivalent to the terms of the claims.

REFERENCE SIGNS LIST 1 heat-exchanger-integrated oxygenator; 7a to 7d, 32, 34 sealing member; 8 heat transfer pipe; 8a, 20a, 30a, 40a, 70a, 98a one end; 8b, 20b, 30b, 40b, 48b, 70b the other end; 10 first header; 20 housing; 21, 41, 71 outer surface; 22 gas inlet port; 24 gas outlet port; 28 blood outlet port; 30 bundle; 40, 40A cylindrical core; 40c 70c central cylinder axis; 40Ha, 40Hb, 60H, 92H, 94H opening; 42 elbow portion; 44, 96L, 96R rib; 44T top portion; 46 support rib; 47 outlet portion; 48 diffusion portion; 48B base portion; 48T protruding portion; 60 second header; 70, 70A, 70B heat exchanger case; 72, 72L, 72R inner surface; 74 heat exchange medium inlet port; 74c, 76c pipe axis; 76 heat exchange medium outlet port; 80, 80A pipe group; 81 circumferential portion; 82 first chord; 83 second chord; 90, 90A to 90E bottom member; 91 direction of normal; 92 outer wall; 92a, 94a end portion; 93 annular wall; 93c inner circumferential surface; 93d outer circumferential surface; 94 inner wall; 95 protrusion; 95a tip end portion; 96 bottom surface; 96a, 96b raised bottom portion; 96c groove portion; 96T projection region; 98 blood inlet port; 98c inside; AR10 to AR17, AR20 to AR24, AR30 to AR36, AR41, AR42, AR71 to AR73, AR71a to AR71c, AR72a to AR72c, AR73a to AR73c, AR90 to AR94, AR96L1, AR96L2, AR96R1, AR96R2, AR99a, AR99b arrow; H1, H2, H72L, H72R distance; S space; S42 gap; W72L, W72R width; and W74, W76 pipe diameter.

The invention claimed is:

1. A multipipe heat exchanger used for extracorporeal circulation of blood, comprising:
    a heat exchanger case;
    a plurality of heat transfer pipes loaded in inside of said heat exchanger case;
    a heat exchange medium inlet port having a shape of a straight pipe, attached to an outer surface on a one end side of said heat exchanger case such that an extension of a pipe axis crosses a central cylinder axis of said heat exchanger case and said extension extends toward the other end side of said heat exchanger case, and supplying a prescribed heat exchange medium to an outer surface of said heat transfer pipe; and
    a heat exchange medium outlet port attached to said outer surface of said heat exchanger case, on a side opposite in a direction of cylinder diameter of said heat exchanger case to a position where said heat exchange medium inlet port is attached, for discharging said heat exchange medium supplied to said outer surface of said heat transfer pipe,
    said plurality of heat transfer pipes in a bundled state having a circumferential portion arranged at a short distance from an inner surface of said heat exchanger case and a first chord which retracts toward a center in the direction of cylinder diameter from an arc formed by said circumferential portion, and
    said plurality of heat transfer pipes in the bundled state being loaded in said inside of said heat exchanger case such that said first chord and said inner surface of said heat exchanger case on a side where said heat exchange medium inlet port is attached are opposed to each other.

2. The heat exchanger according to claim 1, wherein said inner surface of said heat exchanger case on the side where said heat exchange medium inlet port is attached is formed substantially in such a tapered shape as gradually protruding toward the center in the direction of cylinder diameter such that a distance from said first chord is smaller from said one end side of said heat exchanger case toward the other end side of said heat exchanger case.

3. The heat exchanger according to claim 1, wherein said plurality of heat transfer pipes in the bundled state further have a second chord which retracts toward the center in the direction of cylinder diameter from the arc formed by said circumferential portion, on a side opposite in the direction of cylinder diameter to said first chord.

4. The heat exchanger according to claim 3, wherein said inner surface of said heat exchanger case on a side where said heat exchange medium outlet port is attached is formed substantially in such a tapered shape as gradually protruding toward the center in the direction of cylinder diameter such that a distance from said second chord is smaller from said one end side of said heat exchanger case toward the other end side of said heat exchanger case.

5. A heat-exchanger-integrated oxygenator, comprising:
    the heat exchanger according to claim 1;
    a bottom member having a blood inlet port and attached to said one end of said heat exchanger case;
    gas exchange means communicating with the other end of said heat exchanger case, through which said blood that flowed out of the other end of said heat transfer pipe flows; and
    a blood outlet port communicating with said gas exchange means and discharging said blood that flowed through said gas exchange means.

* * * * *